(12) United States Patent
Tromblay et al.

(10) Patent No.: US 6,534,056 B1
(45) Date of Patent: Mar. 18, 2003

(54) THERAPEUTIC AND DIAGNOSTIC USES OF PROTEIN TYROSINE PHOSPHATASE TC-PTP

(75) Inventors: Michel L. Tromblay, Dorval (CA); Maria De Jesus Ibarra Sanchez, Montreal (CA); Paul Daniel Simoncic, Mississauga (CA)

(73) Assignee: McGill University, Montreal Province Quebec (CA)

( * ) Notice: Subject to any disclaimer, the term of this patent is extended or adjusted under 35 U.S.C. 154(b) by 0 days.

(21) Appl. No.: 09/466,992

(22) Filed: Dec. 10, 1999

Related U.S. Application Data

(60) Provisional application No. 60/111,993, filed on Dec. 11, 1998.

(51) Int. Cl.$^7$ .................. A61K 51/00; A61M 36/14; G01N 33/53
(52) U.S. Cl. .................. 424/146; 435/4; 435/7.1
(58) Field of Search .................. 435/7.1, 4; 424/146.1

(56) References Cited

PUBLICATIONS

Champion–Arnaud, et al. (1991), "Activation of Transcription via AP–1 or CREB Regulatory Sites is Blocked by Protein Tyrosine Phosphatases," *Oncogene*, vol. 6:1203–1209.

Cool, et al. (May 9, 1995) Accession No. M25393, "Human Protein Tyrosine Phosphatase (PTPase) mRNA, Complete CDS".

Cool et al. (Jul. 1989), "cDNA Isolated from a Human T–Cell Library Encodes a Member of the Protein–Tyrosine–Phosphatase Family," *Proc. Natl. Acad. Sci. USA*, vol. 86:5257–5261.

Kamatkar et al. (Oct. 25, 1996), "Two Splice Variants of a Tyrosine Phosphatase Differ in Substrate Specificity, DNA Binding, and Subcellular Location," *Journal of Biological Chemistry*, vol. 271(43):26755–26761.

Mosinger et al. (Jan. 1992), "Cloning and Characterization of a Mouse cDNA Encoding a Cytoplasmic Protein–Tyrosine–Phosphatase," *Proc. Natl. Acad. Sci. USA*, vol. 89:499–503.

Radha et al. (1997), "Overexpression of a Nuclear Protein Tyrosine Phosphatase Increases Cell Proliferation," *FEBS Letters*, vol. 409:33–36.

Sherr, Charles (Dec. 6, 1996), "Cancer Cell Cycles," *Science*, vol. 274:1672–1677.

Tiganis et al. (Mar. 1998), "Epidermal Growth Factor Receptor and the Adaptor Protein p52$^{Shc}$ are Specific Substrates of T–Cell Protein Tyrosine Phosphatase," *Molecular and Cellular Biology*, vol. 18(3):1622–1634.

Tillman et al. (May 1994), "Nuclear Localization and cell Cycle Regulation of a Murine Protein Tyrosine Phosphatase," *Molecular and Cellular Biology*, vol. 14(5):3030–3040.

Tonks et al. (May 15, 1988), "Purification of the Major Protein–Tyrosine–Phosphatases of Human Placenta," *Journal of Biological Chemistry*, vol. 263(14):6722–6730.

Yamanashi et al. (Mar. 6, 1997) Accession No. U78818, "Mus Musculus Abl– and p120 rasGAP–Associated Protein Dok (dok) mRNA, Complete CDS".

You–Ten et al. (Aug. 29, 1997), "Impaired Bone Marrow Microenvironment and Immune Function in T Cell Protein Tyrosine Phosphatase–Deficient Mice," *J. Exp. Med.*, vol. 186(5):683–693.

*Primary Examiner*—Sheela Huff
*Assistant Examiner*—Natalie Davis
(74) *Attorney, Agent, or Firm*—Pamela J. Sherwood; Bozicevic, Field, & Francis LLP

(57) ABSTRACT

Cellular sensitivity to DNA damaging agents and progression through cell cycle is modulated through manipulation of T cell protein tyrosine phosphatase (TC-PTP) activity. Phenotypic characterization of cells lacking TC-PTP demonstrates a defective progression through the cell cycle, and sensitivity to DNA damaging agents. Screening assays are provided for selecting agents that affect the activity of TC-PTP, including assays relating to the interaction of TC-PTP with its substrate, p62dok.

15 Claims, 18 Drawing Sheets

|  |  |  |
|---|---|---|
| 0.3% | M1 | 1.0% |
| 66.0% | M2 | 62.0% |
| 4.0% | M3 | 22.0% |
| 22.0% | M4 | 14.0% |

|  |  |  |
|---|---|---|
| 0.3% | M1 | 1.0% |
| 63.0% | M2 | 59.0% |
| 14.5% | M3 | 25.0% |
| 18.5% | M4 | 14.0% |

|  |  |  |
|---|---|---|
| 0.3% | M1 | 2.0% |
| 66.0% | M2 | 50.0% |
| 4.0% | M3 | 29.0% |
| 22.0% | M4 | 17.0% |

|  |  |  |
|---|---|---|
| 0.18% | M1 | 1.0% |
| 25.0% | M2 | 41.0% |
| 43.0% | M3 | 30.0% |
| 20.0% | M4 | 24.0% |

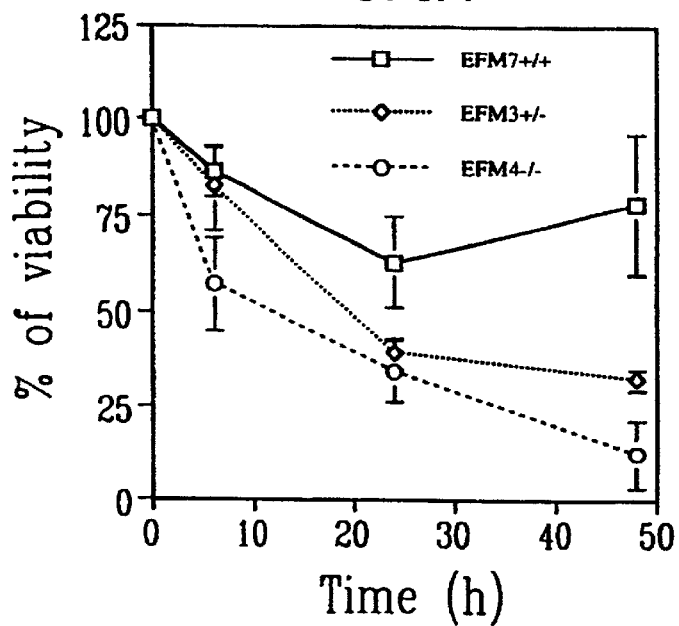
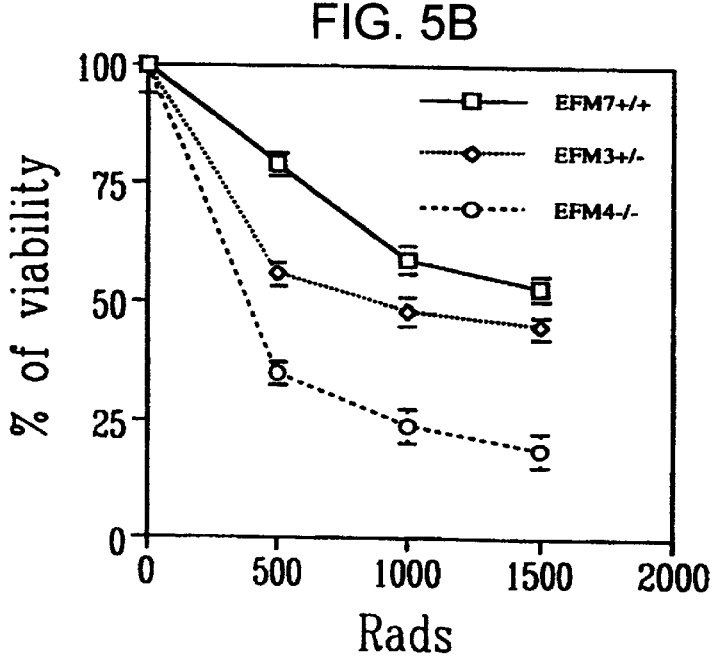

PTAT-HA TC-PTP

PTAT-HA TC-PTP CSDN MUTANT: same as above except for the C215S and D182N changes

THERAPEUTIC AND DIAGNOSTIC USES OF PROTEIN TYROSINE PHOSPHATASE TC-PTP

CROSS-REFERENCE TO RELATED APPLICATIONS

The application claims priority to U.S. provisional patent application No. 60/111,993, filed Dec. 11, 1998.

FIELD OF THE INVENTION

The invention relates to the use of T cell tyrosine phosphatase (TC-PTP) to modulate cellular sensitivity to DNA damaging agents, and to regulate cell cycle.

BACKGROUND OF THE INVENTION

Protein phosphorylation is a common regulatory mechanism used by cells to selectively modify proteins carrying regulatory signals from outside the cell to the nucleus. The proteins that execute these biochemical modifications are a group of enzymes known as protein kinases and protein phosphatases. The first protein tyrosine phosphatase was characterized over a decade ago by Tonks et al. (1988) *J. Biol. Chem.* 263:6722–6730, and since then a great number of other family members have been cloned and biochemically characterized. Yet, the biological function is known for only a few family members.

One of the earliest reported PTP enzymes was the T-cell protein tyrosine phosphatase (TC-PTP). The cDNA encoding the TC-PTP was originally isolated from a human T-cell library (Cool et al. (1989) *Proc. Natl. Acad. Sci.* 86:5257–5261), although it is widely expressed. There are highly related homologues in mouse and rat, under the respective name of MPTP and PTPS (Mosinger et al. (1992) P.N.A.S. 89:499–503; Radha et al. (1997) *FEBS Lett* 409:33–36).

Although TC-PTP was one of the first phosphatases identified, the function(s) of this PTP is unknown. A potential role for TC-PTP in receptor kinase signaling was proposed based on the specific association of the epidermal growth factor receptor (EGFR) and the SHC adaptor protein to the substrate trapping TC-PTP C216S mutant (Tiganis et al. (1998) *Mol. Cell. Biol.* 18:1622–1634). Another aspect of TC-PTP function is suggested by reports that TC-PTP mRNA levels fluctuate in a cell cycle specific manner. TC-PTP mRNA levels appear to increase in G0 and early G1, and decrease for the rest of the cell cycle (Tillmann et al., supra.) On the contrary, the protein levels of the rat PTPS homologue do not appear to vary during the cell cycle, but seemingly changes between nuclear and cytoplasmic compartments. A similar variance in localization was also reported for the human 45 kDa protein.

In a recent publication of the TC-PTP knock-out mouse (You-Ten et al. (1997) *J. Exp. Med.* 186:683–693), it was found that homozygous animals.die between 3–5 weeks of age, in part because of severe anemia due to a failure of erythropoiesis. The TC-PTP–/– mice have a defective microenvironment of the bone marrow resulting from a near absence of stromal cells, and an inability of T and B cells to proliferate following general cell activation by either Concanavalin A or lipopolysaccharides (LPS).

The cell cycle is regulated by a complex network of interacting proteins whose activity is modulated by phosphorylation reactions. This regulation provides a coordinated downstream process leading to DNA: replication. The cell cycle is mainly controlled by two different protein families: the cyclin-dependent kinases (Cdks) and their regulatory subunits, cyclins, Sherr et al. (1996) *Science* 274:1672–1677. The assembly and disassembly of specific cyclin/Cdk complexes are pivotal events driving the cell cycle. Progression through the G1 phase is controlled by two different complexes: cyclin D/Cdk4,6 which is active in early G1, and cyclin E/Cdk2 which is highly active in late G1. The main substrate of both complexes is the product of the retinoblastoma gene, Rb. Rb protein is known as a repressor of the progression toward S phase. Once Rb is phosphorylated in early G1 by cyclin D/Cdk4,6 and by the cyclin E/Cdk2 in late G1, its affinity for E2F transcription factor decreases and initiates transcription of important genes for the S phase.

In the multistep progression of cancer, a normal cell may lose or gain several regulatory cues, thereby leading to its metamorphosis into unregulated proliferation. Included in these changes are signaling events that influence the cell cycle, DNA repair, mitotic and apoptotic properties of the oncogenic cells. In view of the importance of DNA repair and cell cycle regulation in both normal development and the tumorigenic process, the signaling events, mechanism(s) of action, and modulation provided by and placed on TC-PTP are of great interest.

SUMMARY OF THE INVENTION

Methods and compositions are provided for modulating cellular sensitivity to DNA damaging agents through manipulation of T cell protein tyrosine phosphatase (TC-PTP) activity. Also provided are methods of regulating the progression through cell cycle by altering TC-PTP activity. The phenotypic characterization of cells lacking TC-PTP demonstrates a defective progression through the cell cycle, and sensitivity to DNA damaging agents. Screening assays are provided for selecting agents that affect the activity of TC-PTP, including assays relating to the interaction of TC-PTP with its substrate, p62dok.

In one embodiment of the invention, inhibitors of TC-PTP activity are used to induce, sensitivity to DNA damaging agents, e.g. to sensitize susceptible tumors to DNA damaging chemo- or radiation therapy. Inhibitors include dominant negative mutants, inhibitory fragments or mutants of TC-PTP substrate proteins, anti-sense nucleic acids, small molecule inhibitors, and the like.

In another embodiment of the invention, TC-PTP activity is upregulated or otherwise provided to a cell as a protection against DNA damage. Of particular interest is the provision of TC-PTP activity to patients having acute or chronic sensitivity to DNA damage, e.g. ataxia telangiectasia, and other diseases having a defect in DNA repair.

BRIEF DESCRIPTION OF THE DRAWINGS

FIGS. 5A to 5D illustrate the survival of EFM7+/+, EFM3+/– and EFM4–/– cells after DNA-damaging agents.

DETAILED DESCRIPTION OF THE SPECIFIC EMBODIMENTS

Figure 1A:
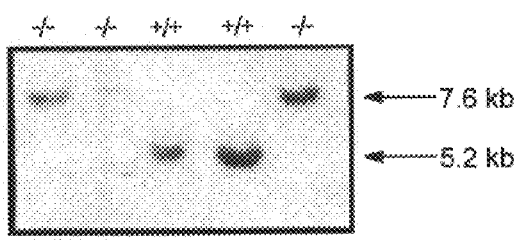
FIGS. 1A to 1D illustrate the isolation of TC-PTP wild-type and knock-out primary murine embryonic fibroblast and cell lines.

The manipulation of T cell protein tyrosine phosphatase (TC-PTP) activity is used to alter cellular sensitivity to DNA damaging agents, and to regulate the progression of cell cycle. The phenotypic characterization of cells lacking TC-PTP demonstrates a defective progression through the cell cycle, and sensitivity to DNA damaging agents. Screening assays are provided for selecting agents that affect the activity of TC-PTP, including assays relating to the interaction of TC-PTP with its substrate, p62dok.

T-cell phosphatase (TC-PTP) is a ubiquitously expressed member of the protein tyrosine phosphatase gene family. Proliferation assays and flow cytometry, demonstrate that TC-PTP−/− fibroblasts and cell lines exhibit a delayed. G1 phase. These cells are also hypersensitive to different DNA damaging agents and display a high incidence of apoptosis. Homologous and non-homologous recombination, which are important mechanisms for the repair of strand breaks, are significantly diminished in the absence of TC-PTP activity. Further, it is shown that a substrate of TC-PTP is p62dok, which is known to be associated with DNA repair responses. Over-expression of TC-PTP is found in a number of carcinoma cells, and detection of TC-PTP levels may be used in diagnostic assays for detecting and staging tumors.

By altering the level of TC-PTP activity in a cell, one can manipulate cell cycle and DNA repair in a targeted cell. By upregulating TC-PTP, cells are made more resistant to DNA damaging agents, such as γ-radiation, UVC radiation, treatment with methyl methane sulfonate, etc. By inhibition of TC-PTP, cells are made more sensitive. The inhibition of TC-PTP also has the effect of delaying cells in G1 phase, which provides a more synchronized cell population for the therapeutic treatment.

Increasing sensitivity of tumor cells to chemotherapeutic drugs and radiation may be desirable, for example to increase the lethality of low-dose radiation or a therapeutic drug. Conversely, decreasing sensitivity of patient bone marrow cells to such drugs or radiation may be highly advantageous. A variety of methods and compositions for altering TC-PTP activity are available. As inhibitors one may administer anti-sense nucleic acids, antibodies or fragments derived therefrom, peptides derived from substrates or other regulatory molecules, and small molecule inhibitors, etc. To enhance activity, TC-PTP can be delivered as a protein, through expression from exogenous nucleic acid constructs, through up-regulation of the endogenous coding sequence, etc.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the kinase" includes reference to one or more kinase proteins and equivalents thereof known to those skilled in the art, and so forth. All technical and scientific terms used herein have the same meaning as commonly understood to one of ordinary skill in the art to which this invention belongs unless clearly indicated otherwise.

T cell protein tyrosine phosphatase: is a mammalian protein tyrosine phosphatase. The sequence of the human TC-PTP coding sequence may be found in Genbank, accession number M25393. TC-PTP was first cloned by Cool et al. supra., who showed that it shares 72% amino acid sequence identity with PTP1B in a 236-amino acid core region present in all PTPases.

The murine enzyme is 93.2% identical to its human homologue, and 95% to PTP1B. In addition to its catalytic domain, TC-PTP contains a non catalytic C-terminal domain that varies in size and hydrophobicity due to alternative splicing. Two major splice forms of TC-PTP have been found in humans and rodents (Champion-Arnaud et al. (1991) *Oncogene*, 6:1203–1209; Mosinger et al. (1992) *Proc. Natl. Acad. Sci.* 89:499–503). These two mRNAs differ at their 3' coding sequence by the use of a donor splice site that results either in the synthesis of a 48 or 45-kDa protein with unique carboxyl termini.

In human cells, the 48-kDa TC-PTP is primarily localized in a fraction of the cell extract that requires treatment with detergent. This 48-kDa TC-PTP contains 19 hydrophobic amino acid residues at the C-terminus that is responsible for the targeting of TC-PTP to the ehdoplasmic reticulum (ER) (Kamatkar et al. (1996) *J. Biol. Chem.* 271:26755–26761). The 45-kDa form lacks the hydrophobic segment at the C-terminus but possesses an eight basic amino acid domain, that contributes to localize the 45 kDa to the nucleus. In addition to the nuclear localization signal (Tillmann et al. (1994) *Mol. Cell. Biol.* 14:3030–3040), it has been reported that the nuclear import factor p97 associates with the carboxyl terminus of the 45 kDa isoform. It has been suggested that the biological function of both forms of TC-PTP might vary according to their localization.

A substrate for TC-PTP is p62dok, which is a 62 kDa protein that is highly phosphorylated in many cells containing activated tyrosine kinases. p62dok has little homology to known proteins, but has a prominent set of tyrosines and nearby sequences suggestive of SH2 binding sites. The sequence of p62dok may be accessed at Genbank, number U78818.

DNA damaging agent: as used herein, means any substance or treatment that induces DNA damage in a cell, including UV irradiation, gamma irradiation, X-rays, alkylating agents, antibiotics that induce DNA damage by binding to DNA, inhibitors of topoisomerases and any compound used in chemotherapy which acts by causing DNA damage. Chemotherapeutic agents contemplated to be of use include VM-26, procarbazine, adriamycin, 5-fluorouracil (5FU), etoposide (VP-16), camptothecin, actinomycin-D, mitomycin C, cisplatin (CDDP), and even hydrogen peroxide. The invention also encompasses the use of a combination of one or more DNA damaging agents, whether radiation-based or actual compounds, such as the use of X-rays with cisplatin or the use of cisplatin with etoposide.

TC-PTP inhibitors: Agents useful for increasing sensitivity to DNA damaging agents are capable of inhibiting TC-PTP. An effective dose will generally inhibit at least about 50% of the phosphatase activity, usually at least about 90%, and may inhibit as much as about 95% or more. The general classes of inhibitors include anti-sense nucleic acids, antibodies, fragments or mutant forms of TC-PTP substrate proteins, and small molecule inhibitors.

Vanadate inhibits protein-tyrosine phosphatases, although vanadium-based phosphatase inhibitors are relatively unspecific. However, the vanadate compounds may be made more specific through the design of ancillary ligands (Posner et al. (1994) *J. Biol. Chem.* 269: 45964604).

Inhibitory compounds may be derived from the sequence of TC-PTP substrates, which include p62dok. Other candidates for interaction with TC-PTP are the DNA repair protein RAD51, and the RNA polymerase II CTD domain, which are c-abl substrates. The criteria for a physiological substrate are that it should be specifically trapped in vitro by the C→S mutant, and be hyperphosphorylated in the −/− cells or in tissues of the homozygous knockout mice.

For example, nonhydrolyzable tyrosine phosphate analogs may be incorporated into a specific peptide substrate, e.g. phosphonomethyl phenylalanine (Zhang et al. (1994) *Biochemistry* 33:2285–2290; difluorophosphonomethyl phenylalanine (Burk et al. (1991) *Synthesis* 11:1019–1020;. L-O-malonyltyrosine (Kole et al. (1995) *Biochem. Biophys. Res. Commun.* 209:817–822); cinnamic acid (Moran et al. (1995) *J. Am. Chem. Soc.* 117: 10787–10788; Cao et al. (1995) *Bioorganic Med. Chem. Lett.* 5:2953–2958; sulfotyrosyl (Liotta et al. (1994) *J. Biol. Chem.* 269:22969–23001). Peptide analogs containing phosphonodifluoromethyl phenylalanine or sulfotyrosyl may be used as a substitute for tyrosine (Chen et al. (1995) *Biochem. Biophys. Res. Commun.* 216: 976–984).

Naturally occurring inhibitors of phosphatases include okadaic acid, tautomycin, calyculin A, thyrsiferyl-23-acetate, cantharidin, microcystin LR, nodularin, motuporin, etc.

Alternatively, one may screen a chemical library for the inhibition of TC-PTP activity. A wide variety of assays may be used for this purpose, including release of labeled phosphate, increase in radiosensitivity, in vitro protein-protein binding assays, electrophoretic mobility shift assays, immunoassays for protein binding, and the like. Of particular interest are.assays that exploit the interaction between TC-PTP and its specific substrates.

The term "agent" as used herein describes any molecule, e.g. protein or pharmaceutical, with the capability of inhibiting the enzymatic activity of TC-PTP. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

Alternatively, antisense molecules are used to down-regulate expression of TC-PTP in cells. The anti-sense reagent may be antisense oligonucleotides (ODN), particularly synthetic ODN having chemical modifications from native nucleic acids, or nucleic acid constructs that express such anti-sense molecules as RNA. Antisense oligonucleotides may be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

The antisense sequence is complementary to the mRNA of the targeted TC-PTP gene, and inhibits expression of the gene products. Antisense molecules inhibit gene expression through various, mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least.about 20 nucleotides in length, and not more than about 500, usually not more than about 50, more usually not more than about 35 nucleotides in length, where the length is governed by efficiency of inhibition, specificity, including absence of cross-reactivity, and the like.

A specific region or regions of the endogenous sense strand mRNA sequence is complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antibodies or binding fragments derived therefrom, e.g. FAb fragments, etc. may be used as inhibitors. Antibodies may be raised to wild-type or variant forms of TC-PTP, to isolated peptides corresponding to domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Enhancers of TC-PTP activity. In most cases, enhancement of TC-PTP activity will result in increased levels of the protein in the targeted cell. The increased protein may be the result of direct introduction of TC-PTP protein or active fragment derived therefrom. Alternatively, expression from the endogenous TC-PTP gene may be upregulated, or an exogenous construct encoding TC-PTP may be introduced into the cell.

Expression vectors may be used to introduce the TC-PTP gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles or mitochondria. Jet injection may also be used for intramuscular administration, as described by Furth et al. (1992) *Anal Biochem* 205:365–368. The DNA may be coated onto gold microparticles, and delivered intradermally by a particle bombardment device, or "gene gun" as described in the literature (see, for example, Tang et al. (1992) *Nature* 356:152–154), where gold microprpjectiles are coated with the protein or DNA, then bombarded into skin cells.

Detection of TC-PTP Expression. Cells, e.g. tumor cells, may be phenotyped by analyzing the level of TC-PTP enzymatic activity, as compared to non-transformed, or normal cell counterparts. Alternatively, the TC-PTP coding sequences may be tested for over-expression. Over-expression, as used herein, refers to cells that express at least two-fold levels above the corresponding non-transformed cell type, usually at least about 5 fold and may be 10 fold or higher. Assays for over-expression may detect levels of the appropriate mRNA, encoded protein, or may utilize a functional assay, e.g. as described in the experimental section. A number of methods are available for analyzing nucleic acids for the presence of a specific sequence, e.g. by hybridization with the sequence to Northern blots, RNA, dot blots, etc., RT-PCR, and the like.

Methods of detecting the presence of a specific polypeptide are also well-known in the art, including ELISA, RIA, affinity-chromatography, etc., where a binding reagent specific for the polypeptide in question is used for quantitation.

METHODS OF USE

Inhibitors of TC-PTP activity are used to induce sensitivity to DNA damaging agents, e.g. to sensitize susceptible tumors to DNA damaging chemo- or radiation therapy. The effect of TC-PTP on cell cycle is also effective in increasing the length of time that cells are in G1 phase, and provides for a more synchronous cell population.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

Tumors, known to be associated with over-expression of TC-PTP genes include colon carcinomas. Other tumors of interest include carcinomas such as prostate, breast, ductal, endometrial, stomach, dysplastic oral mucosa, invasive oral cancer, non-small cell lung carcinoma, transitional and squamous cell urinary carcinoma, etc.; neurological malignancies; e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like. In addition to therapeutic methods, the expression of TC-PTP may be used as a diagnostic to aid in the characterization and staging of tumors.

Inhibitors of TC-PTP are administered to a host suffering from a susceptible tumor. Administration may be topical, localized or systemic, depending on the specific disease. The compounds of the present invention are administered at a dosage that sensitizes the tumor cell population while minimizing any side-effects. It is contemplated that the composition will be obtained and used under the guidance of a physician for in vivo use. The dosage of the therapeutic formulation will vary widely, depending upon the nature of the disease, the frequency of administration, the manner of administration, the clearance of the agent from the host, and the like.

The susceptibility of a particular tumor cell to sensitization and killing may be inferred by the ability to repair DNA damage in biopsied tissue, which may be freshly isolated or fixed, an when possible by in vitro testing, as well. For in vitro testing, cultured cells from a biopsy sample of the tumor are combined with the inhibitor at varying concentrations for a period of time sufficient to allow the inhibitor to act, usually between about 10 minutes and one day. The tumor cells are then irradiated or otherwise treated with DNA damaging agents, and the viable cells left after induction are counted.

In another embodiment of the invention, TC-PTP activity is upregulated or otherwise provided to a cell as a protection against DNA damage. A patient requiring protection from radiation or other DNA damaging treatment is provided with increased TC-PTP activity, as described above.

The TC-PTP modulatory compounds can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The inhibitor may be systemic after administration or may be localized by the use of regional administration, intramural administration, or use of an implant that acts to retain the active dose at the site of implantation.

The compounds of the present invention can be administered alone, in combination with each other, or they can be used in combination with other known compounds. In pharmaceutical dosage forms, the compounds may be administered in the form of their pharmaceutically.acceptable salts, or they may also be used alone or in appropriate association, as well as in combination with other pharmaceutically active compounds.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 ng to 100 milligrams per kg weight of subject per administration. A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the inhibitors may be formulated with other pharmaceutically active agents, particularly other anti-metastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

Following the sensitization procedure, the tumor cells are subjected to a killing dose of DNA damaging agent, e.g. radiation, cisplatin, etc. The dose will vary depending on the specific cytotoxic agent utilized, type of tumor, patient status, etc. and will generally be conventional. Examples of radiation therapy include whole body, hemi-body, and local external beam radiation, or brachytherapy or radioimmunotherapy, at an effective dose that is sufficient to substantially ablate the tumor cell population, while maintaining patient viability. In some cases radiation may be combined with stem cell replacement therapy to reconstitute the patient hematopoietic function.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which scope will be determined by the language in the claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for all relevant purposes, e.g., the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit.the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

Materials and Methods

Murine Embryonic Fibroblast and Cell line Generation. Mouse embryonic fibroblast (MEF) were isolated by trypsinization of littermate embryos dissected at 14 days of gestation from a cross of heterozygous TC-PTP mutant mice. Each embryo was harvested separately, the brain and internal organs were removed and the carcasses were minced and incubated with trypsin for 30–45 min at 37° C. Homogeneous cell suspension were plated in 10 cm dish in Dulbecco's modified Eagle's medium (DMEM) supplemented with 10% fetal bovine serum (FBS). Experiments with MEF were performed in early passage (P6). Cells were expanded every 3 days until spontaneous cell lines were obtained. Genotyping was established by Southern blot analysis, as described previously (You-Ten et al., supra.)

G0 synchronization. $10^6$ cells were plated in a 10-cm dish and grown to confluence in DMEM supplemented with 10% FBS for 4 days. Fibroblasts were washed with PBS twice and incubated for 2 days with DMEM with 0.1% of FBS.

Cell proliferation and survival. Primary MEF+/+ and −/−, and TC-PTP+/+ and TC-PTP−/− cell, lines were seeded in 24-well cell culture plates at a density of cells/cm$^2$ in DMEM with 10% FBS. Cell number was determined after trypsinization by trypan blue exclusion or by MTT assay (Mosmann (1983) *J. Immunol. Methods*. 62:55–63) at day 1, 3, 5 and 7 after plating. Cells were treated with gamma- or UV-irradiation at doses indicated using a Gammacell 1000 (Atomic Energy of Canada) with a 137Cs source and Stratalinker (Stratagene) respectively. After irradiation, the cells were plated in triplicate on 24-well plates. Survival was evaluated by MTT viability assays 48 hr post-radiation.

Cell cycle analysis. Synchronized cells were washed with PBS, trypsinized and seeded at $1\times10^4$ cell/cm$^2$ in a 10-cm dish with DMEM+10% FBS. Cells were harvested by trypsinization at the time indicated, and fixed with 4% paraformaldehyde for 30 min. They were then washed with PBS and kept in 70% ethanol overnight at 4° C. Cells were centrifuged at 2000 rpm and incubated at 37° C. in PBS containing 2 $\mu$/ml of RNase A (Boehringer Mannheim). Cells were stained with propidiumn iodide (PI; Sigma Chemical Co.) at a final concentration of 0.2 mg/ml. The samples were processed by FACScan (Becton Dickinson).

Immunoblotting: Wild-type and knock-out TC-PTP cell lines were lysed with 0.1% NP-40, 125 mM NaCl, 25 mM Tris HCl pH 7.2 containing protease inhibitor cocktail (Complete, EDTA-free; Boehringer Mannheim). 50 $\mu$g of protein were fractionated by SDS-PAGE and transferred to Immobilon-P PVDF membranes (Millipore Corp., Bedford, Mass.). Membranes were blocked in TBS-T (10 mM TrisHCl [pH 7.5], 150 mM NaCl, 0.03% of Tween 20) containing 5% nonfat dry milk. TC-PTP was detected using mouse anti-TC-PTP (clone 3E2; You-Ten et al., supra.) For the detection of the cell cycle proteins the following commercially available antibodies were used; rabbit anti-cyclin E; rabbit anti-Cdk2 (Santa Cruz Biotechnology), and mouse anti-Rb (PharMingen G3-245). A secondary goat antibody against mouse or rabbit IgG conjugated to horseradish peroxidase (Jackson Immunoresearch) were used. Detection was performed by chemiluminescence (NEN Life Science Products).

In vitro recombination assay: For the in vitro recombination assay, a 0.5 $\mu$g each of pBR322-D1 and pBR322-2 plasmid DNA were mixed with 30 $\mu$g of protein in 100 $\mu$l of reaction mix (20 mM Tris-HCl, pH 7.5, 10 mM MgSO$_4$, 85 mM NaCl, 1 mM ATP, 100 $\mu$M each dNTPs and 0.001% gelatin). The reaction was incubated 60 min at 37° C. and stopped by addition of 25 mM EDTA and 100 $\mu$g/ml of pronase. The DNA was phenol-chloroform extracted, and ethanol-precipitated at −80° C. for 45 min. The DNA was resuspended in MCT buffer (10 mM MgCl$_2$, 10 mM CaCl$_2$, 10 mM Tris-HCl, pH 7.5) and used to transform DH1 or DH5 cells. The numbers of ampicillin- and tetracycline-resistant colonies was determined and the recombination frequency calculated accordingly.

In vitro non homologous end jointing assay. The non homologous end jointing activities were determined by utilizing a method similar for the one described for the recombination assay. The substrate in this assay was the pBR322-D2 that was linearized with the restriction endonuclease EcoRV.

RESULTS

Figure 1B:
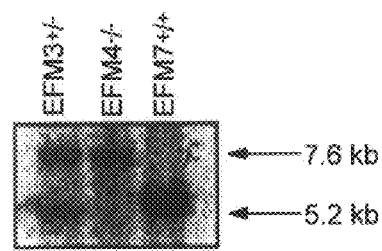

Establishment of TC-PTP+/+ and -TC-PTP−/− murine embryonic fibroblast. To define the biological function of TC-PTP in cellular proliferation, we isolated wild type and TC-PTP−/− murine embryonic fibroblasts (MEF) from 14 day old embryos. Primary MEFs were used only from the six initial passages, and were maintained in culture to obtain spontaneous cell lines. Genotyping of the primary MEF and the cell lines was performed by Southern blot analysis, the upper band of 7.6 kb represents the knock-out TC-PTP allele and the wild-type allele is shown by lower band of 5.2 kb (FIGS. 1A, B). Primary murine embryonic fibroblast and cell lines of wild-type (+/+), heterozygous (+/−) and knock-out (−/−) rigins were established as described in materials and methods. (FIG. 1A) Genotyping of primary MEF, genomic DNA from primary MEF generated from different embryos was digested with Bgl II and transferred to Hybond N$^+$ for Southern blot analysis. (FIG. 1B) Genotyping of EFM7+/+, EFM3+/− and FFM4−/− cell lines was done as in A.

Figure 1C:
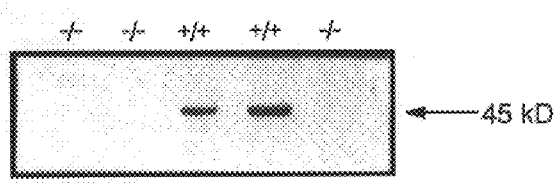
Figure 1D:
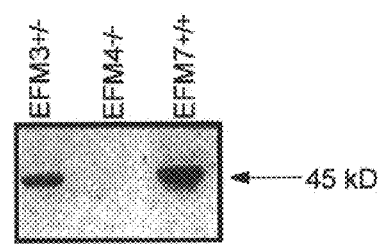

We confirmed the complete absence of the protein in the TC-PTP−/− cells using immunoblotting with a monoclonal antibody against TC-PTP. There is a complete absence of the 45 kDa band in the TC-PTP−/− in primary MEF and cell lines (FIGS. 1C, D). (FIG. 1C) Western blot analysis of primary MEF. Protein samples from primary MEF were extracted and equal amounts of protein (25 $\mu$g) were loaded on 10% SDS-PAGE and immunoblotted with anti TC-PTP antibody. (FIG. 1D) Western blot analysis of EFM7+/+, EFM3+/− and EFM4−/− cell lines was performed as in C.

Figure 2A:
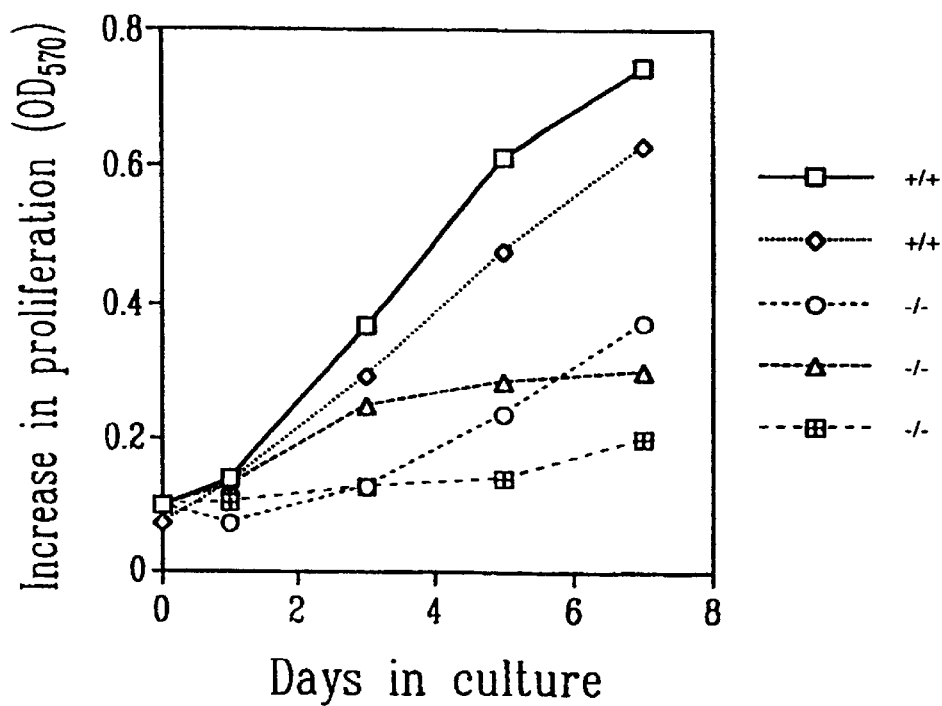
FIGS. 2A and 2B illustrate the comparison of the growth rate for TC-PTP+/+, TC-PTP+/– and TC-PTP–/– primary MEF and cell lines.

The primary MEF and cell lines were tested in proliferation assays using MTT or trypan blue exclusion. The results indicate that the TC-PTP−/− primary MEF have a much slower proliferation rate than the TC-PTP+/+ cells (<30%) (FIG. 2A). Wild-type, heterozygous and knock-out primary MEF and cell lines were'seeded in 24-well cell culture plates at $1\times10^4$ cells/cm$^2$, and incubated in DMEM with 10% of fetal bovine serum. (FIG. 2A) Proliferation of two TC-PTP+/+ and three TC-PTP−/− MEF was evaluated by reduction of MTT at 1, 3, 5 and 7 days after plating. Results are shown as the average of triplicate plates. (FIG. 2B) Proliferation rate of the EFM7+/+, EFM3+/− and EFM4−/− cell lines was evaluated by counting cell number after trypsinization. These experiments were repeated three times and all gave similar results. The result of a representative experiment is shown.

Figure 2B:
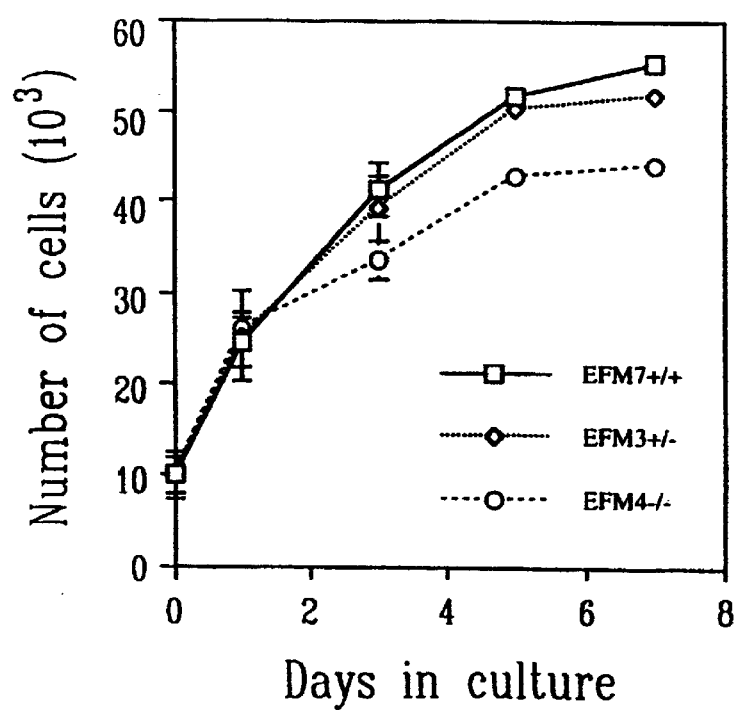

Similar results were obtained with the established cell lines EFM7+/+ and EFM4−/−. We also observed that the heterozygous cell line EFM3+/− had a behavior similar to the EFM7+/+ cell lines (FIG. 2B).

TC-PTP−/− cells show altered G1 regulation: In order to explore if the slower proliferation of the TC-PTP−/− cells affects one particular phase of the cell cycle, we evaluated the cell cycle progression in EFM7+/+ and EFM4−/− cells by fluorescence activated cell sorter (FACS) analysis.

Interestingly, EFM4−/− cells present a longer G1 phase compared to the EFM7+/+ cells (FIGS. 3A–G). Synchronized cell lines were trypsinized and seeded in 10 cm-dish at $1\times10^4$ cells/cm$^2$ with DMEM plus 10% of fetal bovine serum. Cells were trypsinized 0, 12, 16, 20, 24, 28, and 32 hours after plating. Cells were fixed with 4% paraformaldehyde, stained with 0.2 µg/ml of propidium iodide, and analyzed by FACS. The areas shown are M1 (Sub G1), M2 (G1), M3 (S), M4 (G2-M).

Figure 3A:
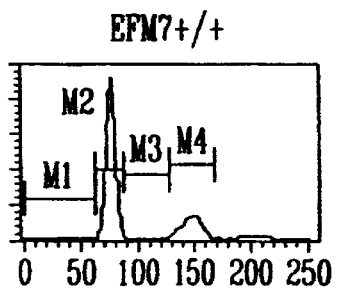
FIGS. 3A to 3G illustrate cell cycle progression of EFM7+/+ and EFFM4–/–.
Figure 3A:
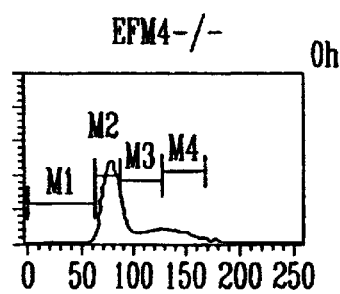
Figure 3B:
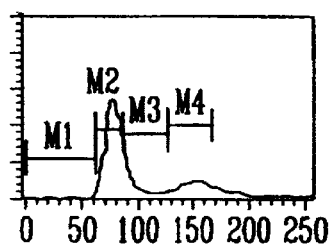
Figure 3B:
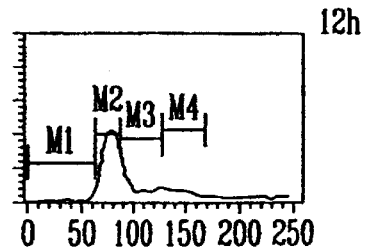
Figure 3C:
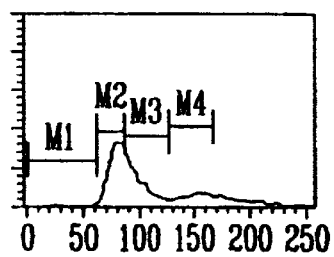
Figure 3C:
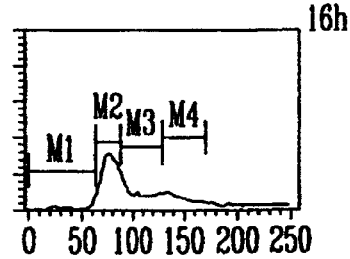
Figure 3D:
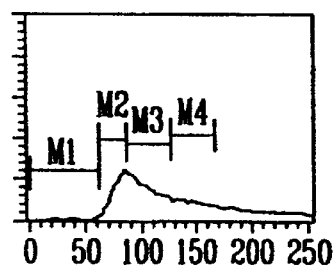
Figure 3D:
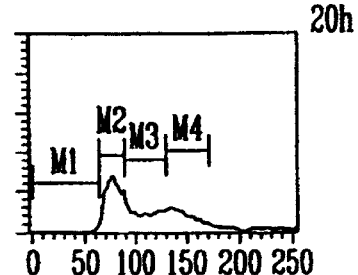
Figure 3E:
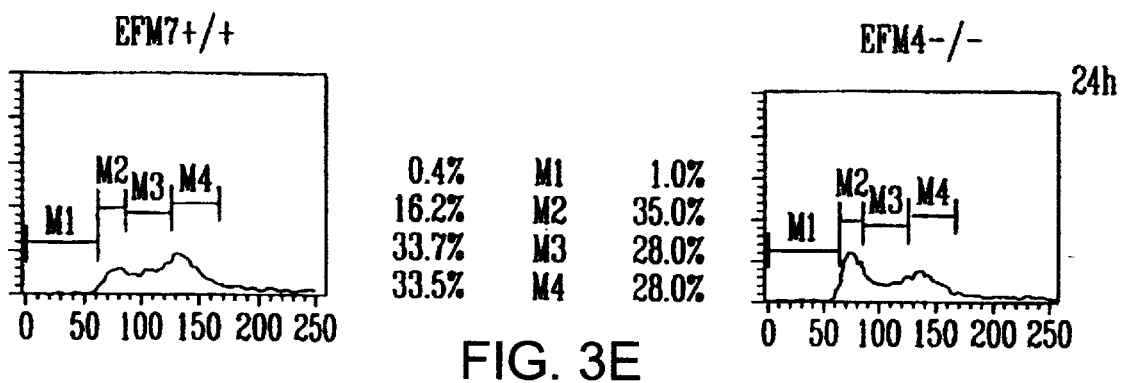
Figure 3F:
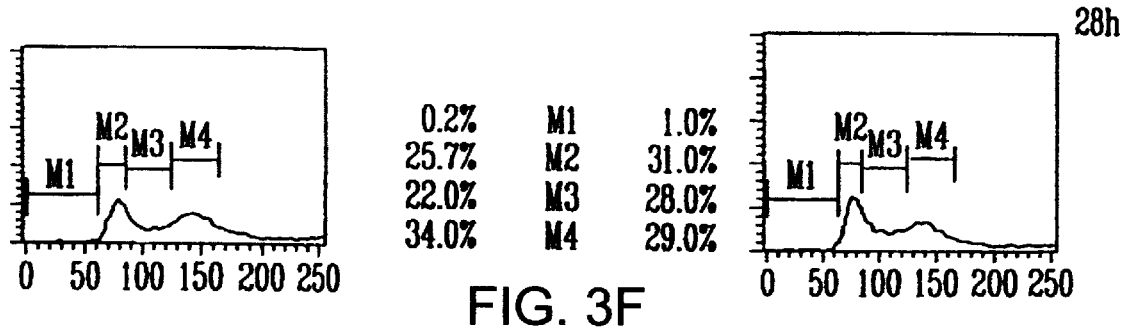
Figure 3G:
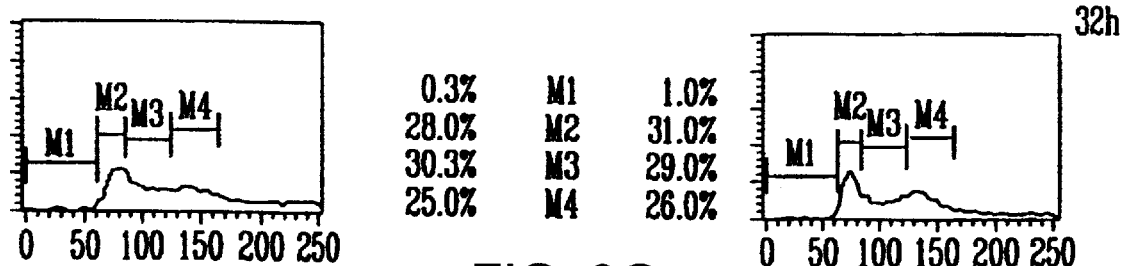

This is particularly evident at 20 and 24 hours after the start of the cell cycle. At these points: of the cell cycle, 25% and 16% of EFM7+/+ cells, compared to 41% and 35% of the EFM4−/− cells population were in G1 respectively (FIGS. 3D and E). At 28 h; we observed that the segment of EFM7+/+ cells in G1 increased again, indicating that these cells were entering in a second cycle. Meanwhile the corresponding EFM4−/− population was still in the G1 phase with a continued increase in the population appearing in S phase (FIG. 3F). No significant differences were found in the sub-G1 (M1) portion of the scan suggesting that the cell population of either genotype does not display any significant apoptotic events.

Figure 4A:
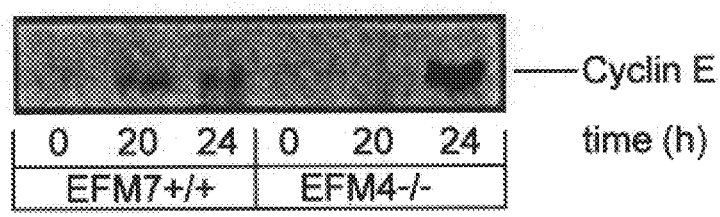
FIGS. 4A and 4B illustrate the immunoblot analysis of cyclin E, Cdk2 and Rb proteins in EFM7+/+ and EFM4–/–.

G1 progression is controlled by an intricate system of protein-protein interactions and phosphorylation reactions between cyclin dependent kinase (Cdk's) and their respective cyclin-associated partners. In early G0 to early G1 transition cyclin inhibitors must be inactivated and cell cycle promoting CDK's such as CDK4 must be activated. In order to verify the proper activation of the cell cycle, we measured by western blotting the appearance of cyclin D1 and the disappearance of the cell cycle inhibitor p27KIP1 (FIG. 4A) from cells that were synchronized by serum withdrawal, and trigger to enter the cell cycle by readdition of 15% FCS. In wild-type cells, cyclin D1 increases from 0 to 8 hrs after serum stimulation, in synchrony with the disappearance of the inhibitor p27KIP1 at 12 hours of post serum treatment. In contrast, the TC-PTP−/− cells present a decrease in the level of the newly made cyclinD1 and a delay in the disappearance of the cell cycle inhibitor p27KIP.

Figure 4B:
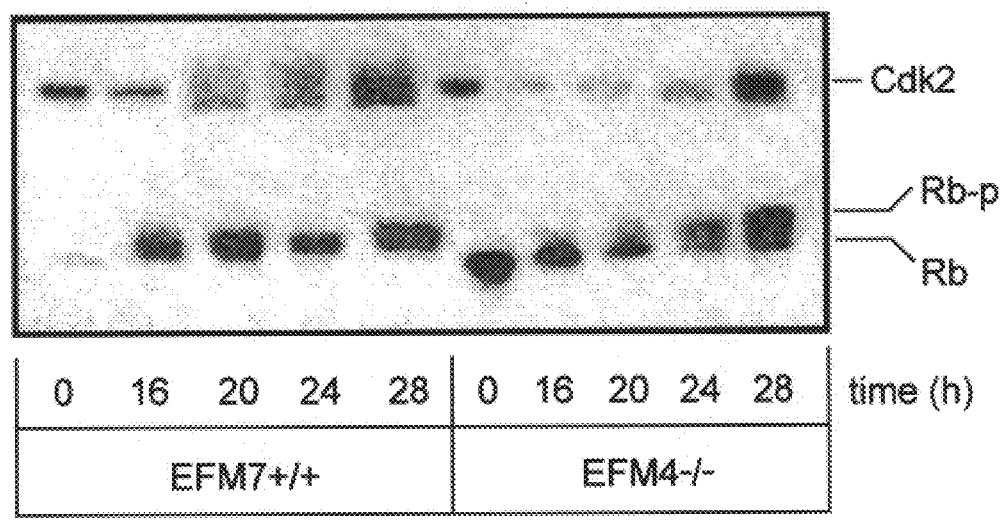

To further explore the molecular mechanism of G1 failure in the TC-PTP−/− cells, we evaluated three important markers for the transition G1/S of cell cycle progression; the expression of cyclin E, and the activation by phosphorylation of Cdk2 and Rb. At various time points of the cell cycle, proteins from synchronized EFM7+/+ and EFM4−/− cells were subjected to western blot analysis with anti-cyclin E antibody. Cyclin E expression occurs only in late G1 leading to the activation of Cdk2. The results show a delayed expression of cyclin E in EFM4−/− cells, meanwhile in EFM7+/+ occurred at 20 h in the EFM4−/− was 24 h (FIG. 4B). Equal amounts of protein. (25 µg) of synchronized EFM7+/+ and EFM4−/− were harvested at 0, 16, 20, 24 and 28 hour after starting the cell cycle. Protein samples were resolved by 12% SDS-PAGE and immunoblotted with anti-Cdk2 or cyclin E. For the Rb, protein was separated in a 7.5% SDS-PAGE and immunoblotted with anti-Rb (FIG. 4B).

The phosphorylated modified form of Cdk2 (lower band representing active Thr-160 phosphorylated form; Gu et al., 1992) in the EFM7+/+ showed an increased electrophoretic mobility at 20 h, meanwhile the activated form of Cdk2 in EFM4−/− cells was detectable until 28 h (FIG. 4). Finally, in accordance with the delay of Cdk2 activation, the hyperphosphorylated form of Rb protein is also delayed in EFM4−/− cells versus the EFM7+/+ cells (FIG. 4). Together, these results confirm that the absence of TC-PTP correlates to a major delay in the cell cycle progression of mammalian cells and that this delay appears to occur at the G0 to early G1 transition of the cell cycle.

Hypersensitive Response of TC-PTP−/− Cells to DNA Damaging Agents

The function of cell cycle checkpoints is to verify the physical status of the genomic DNA. For example, in response to DNA damage, the cell cycle is blocked at the G1/S or G2/M transitions, in part to allow the affected cells to repair the DNA damage before pursuing DNA replication, or entry into mitosis. To assess the effects of DNA-damaging agents such as γ-radiation, UV-C radiation and methyl methane-sulfonate (MMS) treatment on TC-PTP−/− cells, we first evaluated at different times after treatment, the effect of 1000 rads of γ-radiation on the survival of the EFM7+/+, EFM3+/− and EFM4−/− cells. Cells ($1\times10^4$ cells/cm$^2$) were treated with 1000 rads of γ-radiation. Conversion of MTT was evaluated as a measure of survival at 8, 24 and 48 h after the treatment and it is expressed as the percentage of OD570 measurements of treated to untreated wells. Standard-errors derived from three independent experiments are indicated.

Figure 5C:
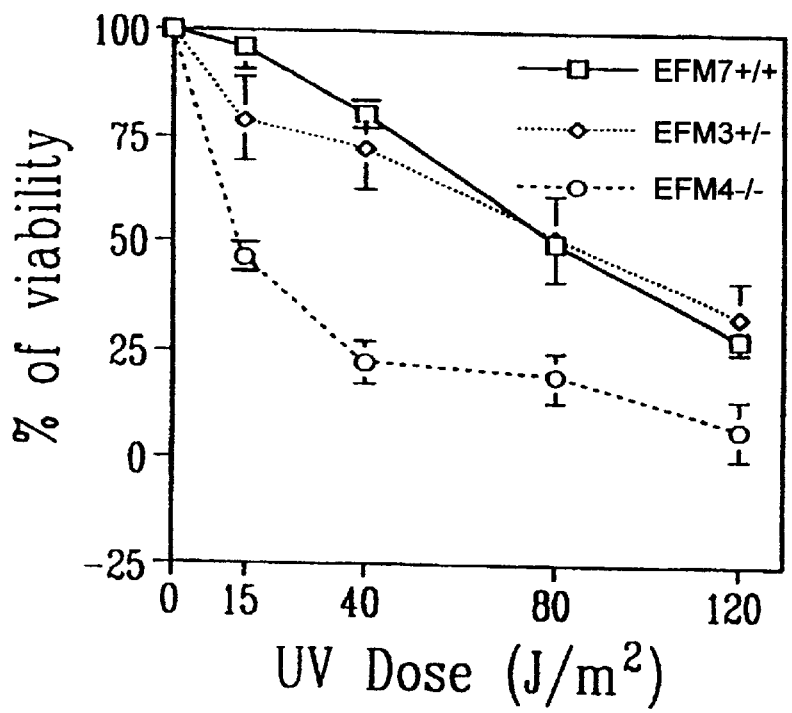

As shown in FIG. 5A, the EFM4−/− cells were hypersensitive to γ-radiation compared with the counterpart EFM7+/+. Even at lower irradiation dose of 500 rads, only 30% of the EFM4−/− cells survived, showing greater hypersensitivity. It may be noted that at 48 h the EFM7+/+ appears to recuperate meanwhile the EFM4−/− continues to decrease in viability. This could be likely due to a failure in the EFM4−/− cells to respond to DNA damage. In comparison, the viability of both EFM7+/+ and EFM3+/− cells showed a much slower decrease with the increase inirradiation dose (FIG. 5B). Furthermore, the heterozygous cell line EFM3+/− displayed an intermediate sensitivity at all doses and times compared with the EFM7+/+ (FIGS. 5A, B).

We examined the response of EFM7+/+, EFM3+/− and EFM4−/− to UV-C treatment. In this assay EFM7+/+ remain completely viable following a 15 J/m2 UV-C treatment. On the contrary, the EFM4−/− presented a 50% decrease in the viability of the total population (FIG. 5C) after 48 hours.

Figure 5D:
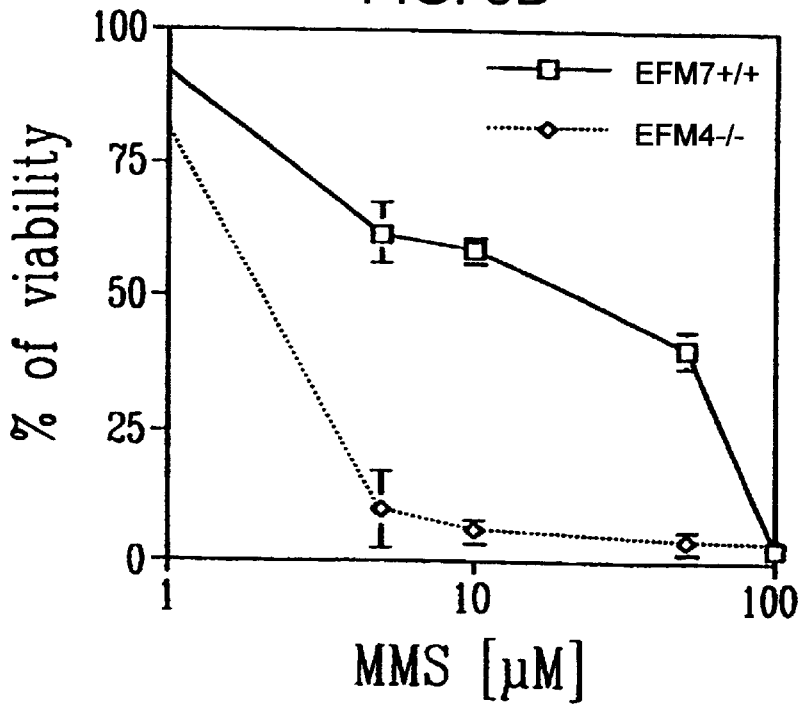

Another DNA-damaging agent used was MMS, which is a DNA alkylating agent that results in single-strand breaks. EFM7+/+ and EFM4−/− were treated with different doses of MMS. EFM4−/− showed a strong decrease in the viability at a concentration as low as 5 µM, compared with slight decrease observed in EFM7+/+ at the same concentration of MMS. Eventually the increase in concentration of MMS becomes highly toxic for the cells, perhaps due to an abundance of DNA damage and they are induced to cell death (FIG. 5D). Survival of EFM7+/+ and EFM4−/− was evaluated 24 h after treatment with range dose of methyl methane-sulfonate. Results are expressed as in A.

Figure 6A:
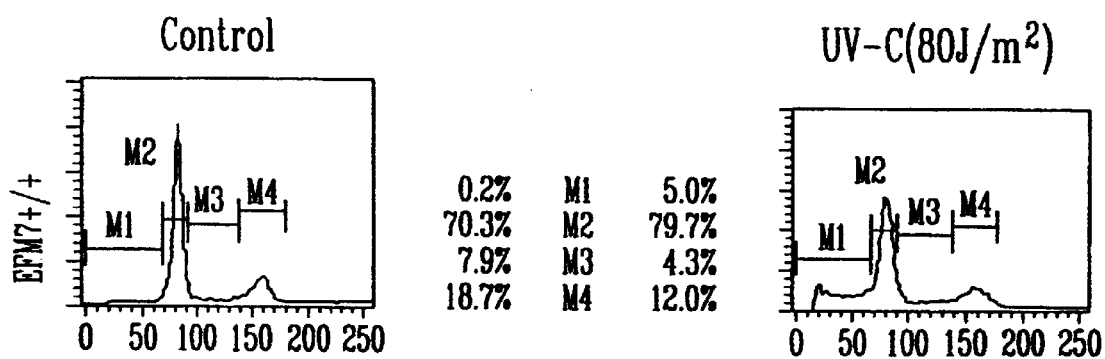
FIGS. 6A and 6B illustrate the induction of apoptosis in EFM7+/+ and EFM4–/– after UV-C treatment.
Figure 6B:
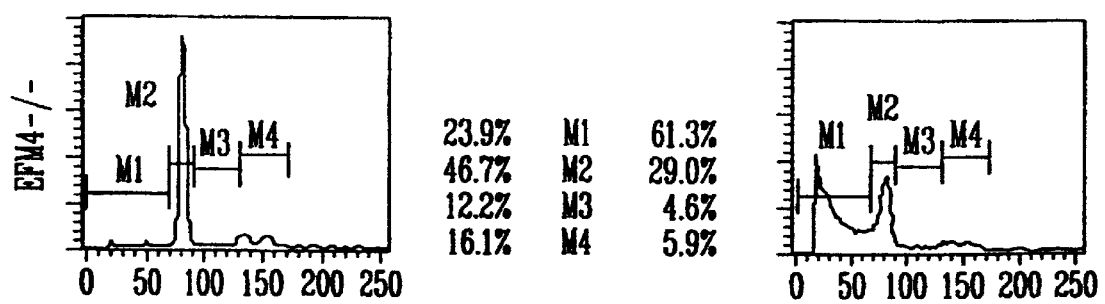

These results confirm that the TC-PTP−/− cells are hypersensitive to different agents that cause breaks in the DNA. To test whether TC-PTP−/− cell death occurred through apoptosis, UV-C treated cells were stained with propidium iodide and examined by FACS analysis. In this assay apoptotic cells typically appears as a sub-G0/G1 peak. After treatment with 80 J/m$^2$ of UV-C, 61% of the EFM4−/− population were induced to apoptosis. (represented by the subG1/M2) compared with 5% induced in EFM7+/+ cells (FIG. 6). Synchronized cell lines were trypsinized and seeded in 10 cm-dish at $1\times10^4$ cells/cm$^2$ in DMEM plus 10% of fetal bovine serum. Cells were trypsinized and treated with 80 J/m$^2$ of UV-C. For time 0 cells were fixed just after trypsinization. Cells were seeded after the treatment and harvested after 24 h by trypsinization. Cells were fixed with 4% paraformaldehyde, stained with 0.2 μ/ml of propidium iodide, and analyzed by FACScan.

These data suggests that the expression of the TC-PTP enzyme in mammalian cells is necessary for an optimal protection against DNA-damaging agents.

Figure 7:
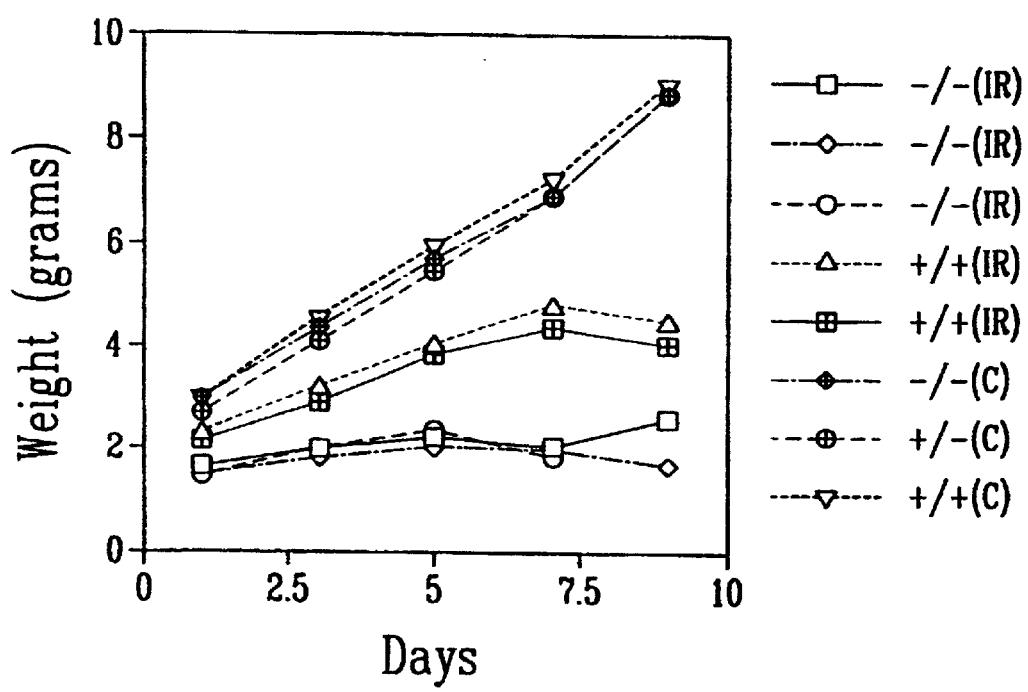
FIG. 7 illustrates the hypersensitivity of TC PTP−/− mice to γ-radiation.

TC-PTP−/− mice are hypersensitive to γ-radiation. We have previously reported that TC-PTP−/− mice show 100% lethality between 3–5 weeks, probably due to a defect in bone marrow function and its associated severe anemia (You-Ten et al., supra.) To verify if TC-PTP−/− homozygous animals were sensitive to irradiation, we subjected homozygous and wild type animals to 100 rads of γ-radiation within 24 hr after birth. Following irradiation, mice were placed under observation and they were weighed every third day. TC-PTP−/− mice quickly became moribund after the fifth day postirradiation and they died after the ninth day. The irradiated wild type animals did hot show the dramatic retardation in growth as the irradiated TC-PTP−/−, by comparison to the unirradiated mice (FIG. 7). Wild type and TC-PTP−/− mice were irradiated with 100 rads within the 24 hr after birth by using a 137Cs source. Unirradiated wild type, TC-PTP+/− and TC-PTP−/− mice are shown for comparison. Weights of individual animals are plotted against time. TC-PTP−/− mice died subsequently at day 7 postirradiation. These results confirm that the homozygous TC-PTP−/− mice also display a dramatic susceptibility to γ-irradiation, a phenomenon identical to those exhibited by TC-PTP−/− fibroblasts.

TC-PTP−/− cells display deficient DNA repair. Genotoxic agents like ionizing radiation, UV light and MMS are known to induce severe damage in DNA. To repair these lesions, irradiated cells counteract by.activating DNA repair machinery. The irradiation sensitivity of the TC-PTP−/− cells, and homozygous animals, as well as the altered G1 cell cycle detected in the TC-PTP−/− cells, led to a characterization of the status of DNA repair machinery in TC-PTP deficient cells. We used in vitro assays of homologous recombination and non-homologous ends joining (NHEJ) to test the ability of TC-PTP+/+ and TC-PTP−/− to rejoin broken DNA strands. In three independent experiments, the results indicate that TC-PTP−/− cells are reduced in double strand/single strand (ds/ss), and double strand/double strand DNA recombination process, as it is shown in the homologous recombination assays (Table 1). In the NHEJ assay, the TC-PTP−/− cells also presented less events compared with the TC-PTP+/+ cells (Table 1). These results suggest that the delay in the transition G1/S as well as the hypersensitivity to DNA-damaging agents of TC-PTP−/− cells may be caused by their inability to repair DNA. Hence, these results strengthen a model whereby TC-PTP acts at least in part to protect cells against DNA damage.

Figure 8A:
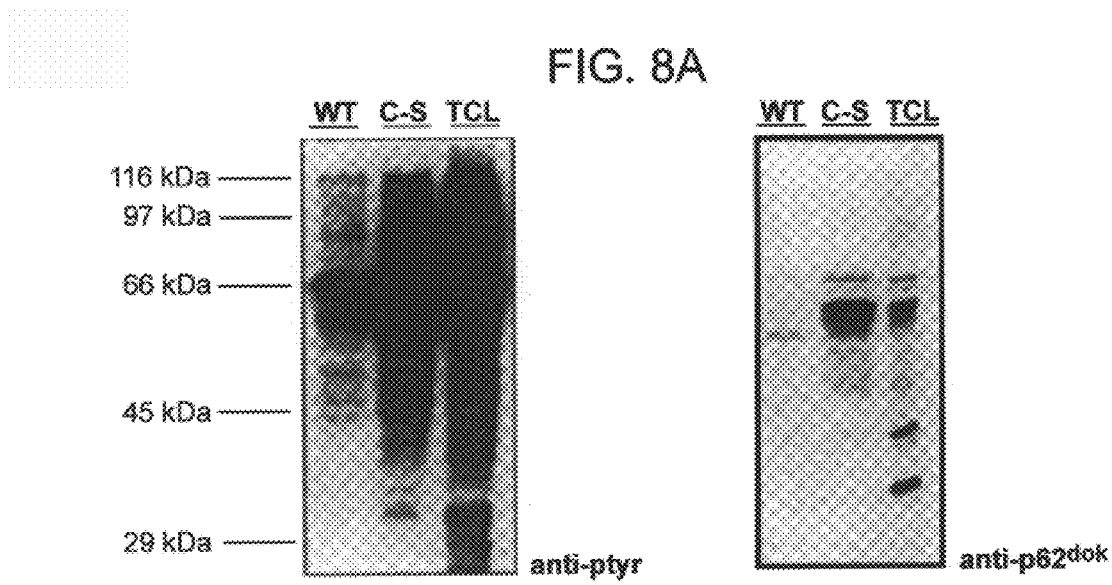
FIGS. 8A and 8B illustrate the use of the TC-PTP−/− mouse and substrate trapping for finding physiological TC-PTP substrates, as shown for the protein p62DOK.
Figure 8B:
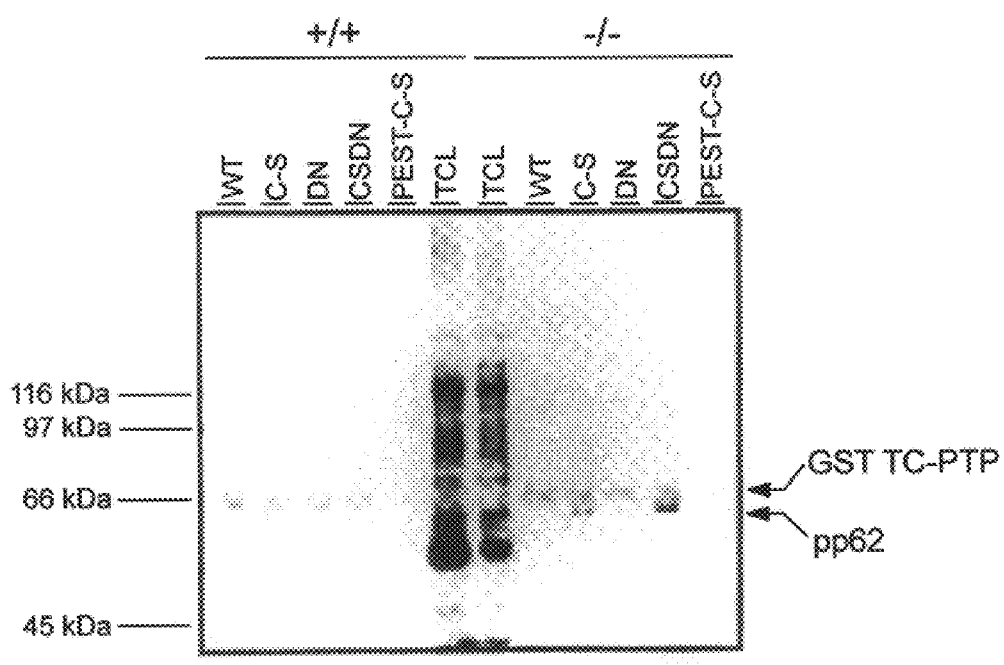

TC-PTP C-S trapping in −/− cells demonstrate binding to p62dok. The substrate trapping technique allows identification of substrates of protein tyrosine phosphatase's. When src transformed cell extract are used with a catalytically inactive C→S GST-TC-PTP mutant, a protein of 62 kDa becomes associated with the mutant. This protein has been identified as p62dok by western blotting (FIG. 8a). This protein is associated with several signaling pathways, including those downstream of the DNA repair response. The generation of TC-PTP−/− mice provides a particularly good system for improving the C→S substrate trapping, using the methods as described by Coté et al. (1998) Biochemistry 37(38):13128–37. When TC-PTP−/− spleen extract is used for substrate trapping technique with catalytically deficient TC-PTP C→S, TC-PTP D→N or TC-PTP CS→DN mutants, at least one protein of 62kDa becomes hyperphosphorylated on tyrosine in the knock out extracts in comparison to wt derived spleen extract (FIG. 8b). These results suggest that non only −/− cells allows the identification of at least one physiological substrate of TC-PTP but that specific substrate is involved in a DNA repair signalling. pathway.

Figure 9A:
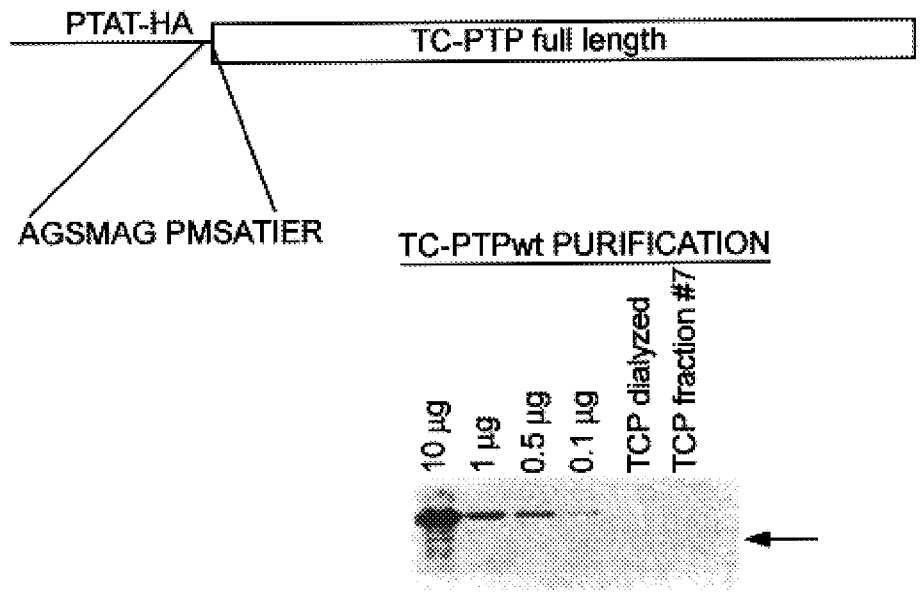
FIGS. 9A and 9B illustrate the constructs use in the bacterial production of the tat-TC-PTP vector system to deliver the wt or CS-DN TC-PTP mutants.
Figure 9B:
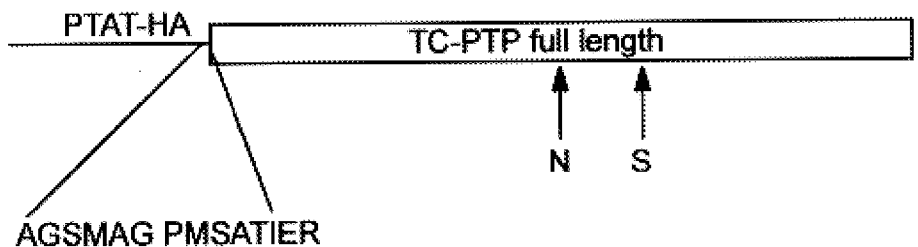
Figure 10:
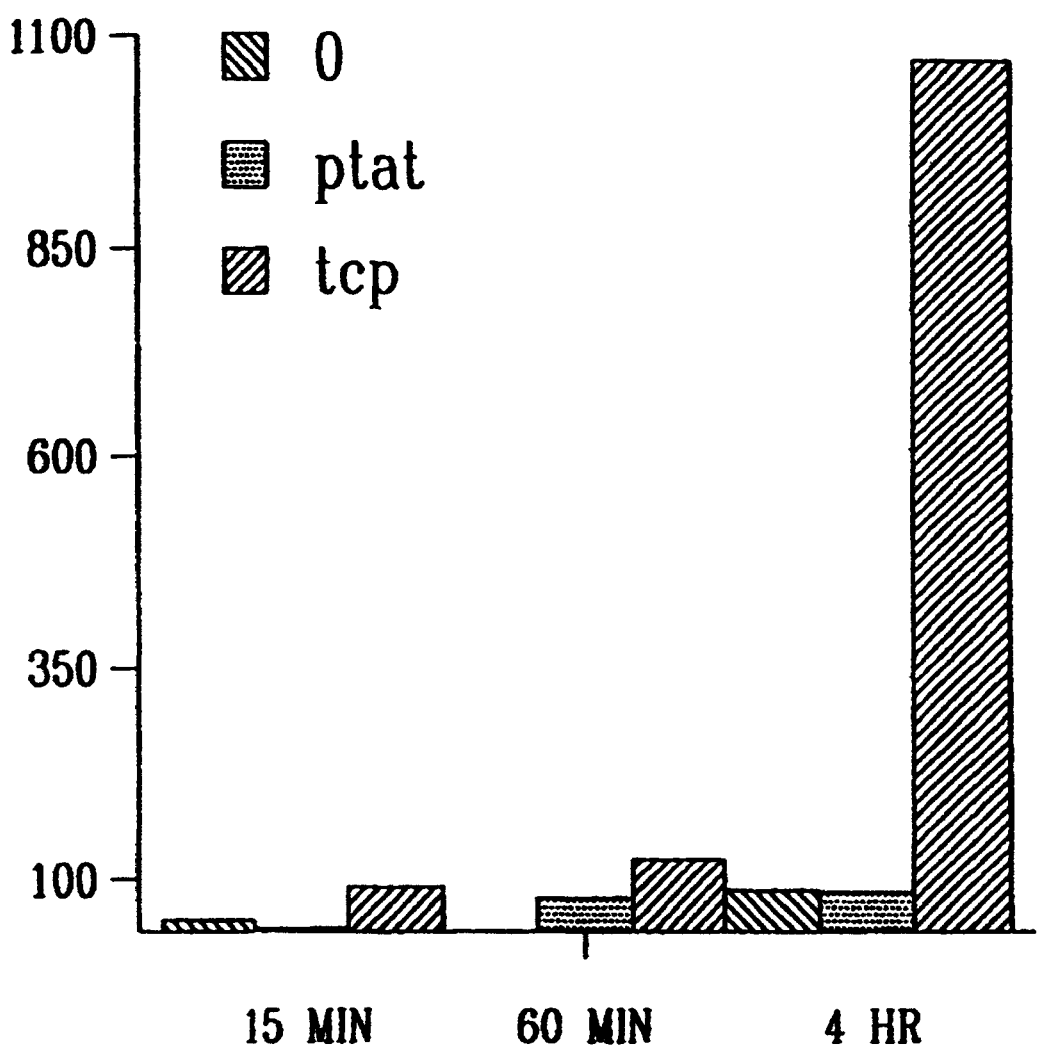
FIG. 10 illustrates that the tat-TC-PTP proteins can rapidly deliver a PTP enzymatic activity into cell extracts of human cancer cells.
Figure 11:
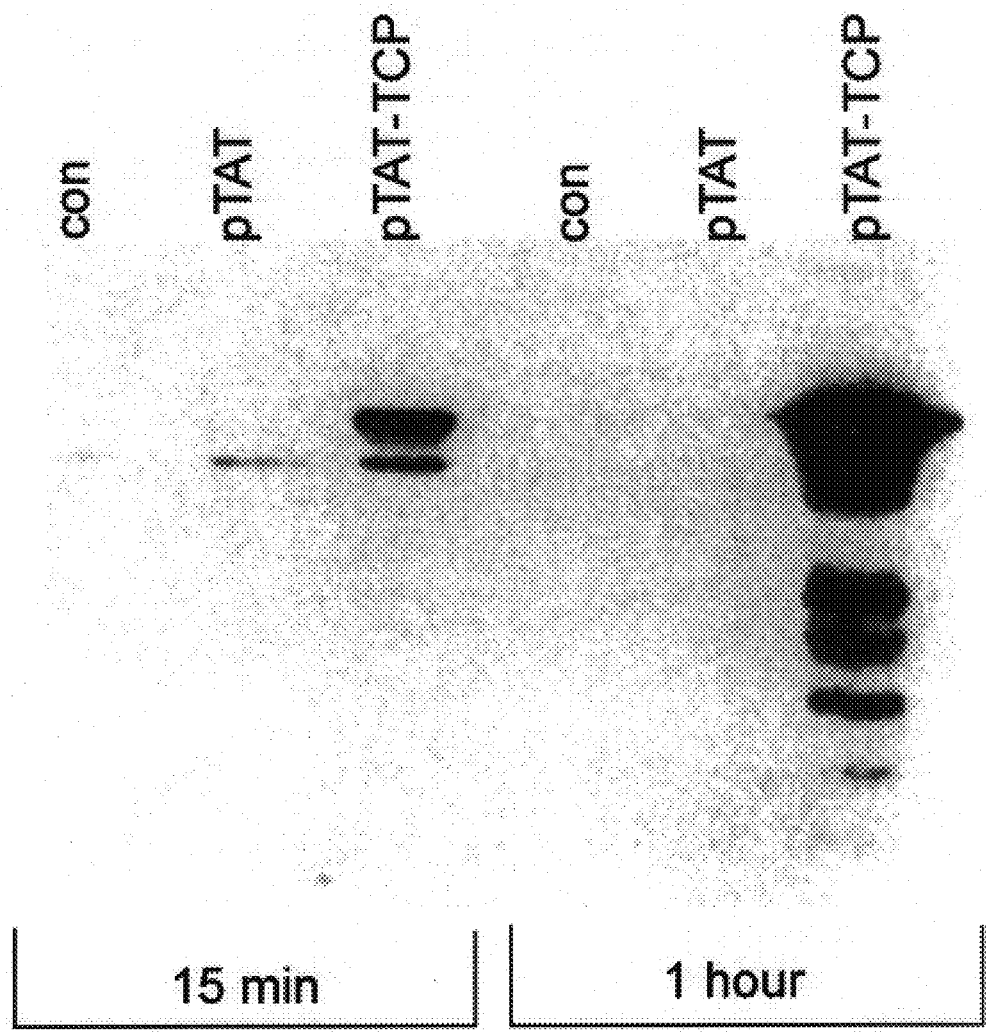
FIG. 11 illustrates the presence of tat-TC-PTP fusion proteins into mammalian cells.
Figure 12A:
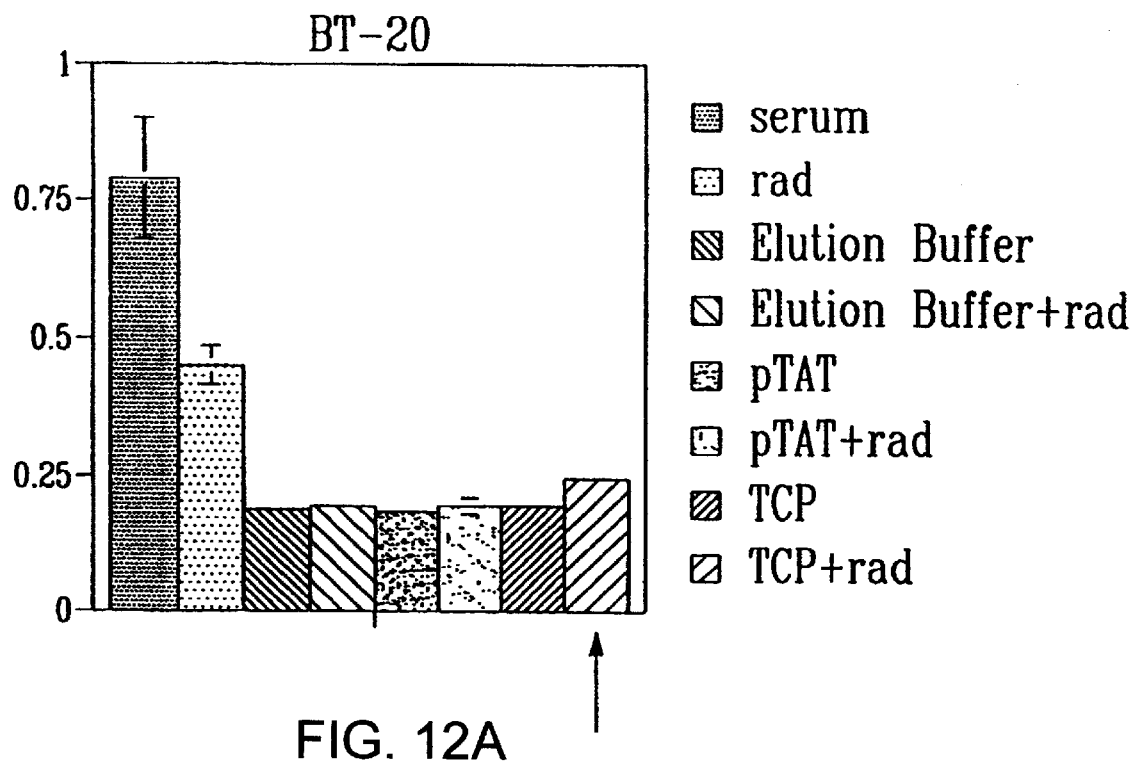
FIGS. 12A to 12D illustrate the radioresistance that can be deliver to mammalian cells by expressing exogenous TC-PTP proteins.
Figure 12B:
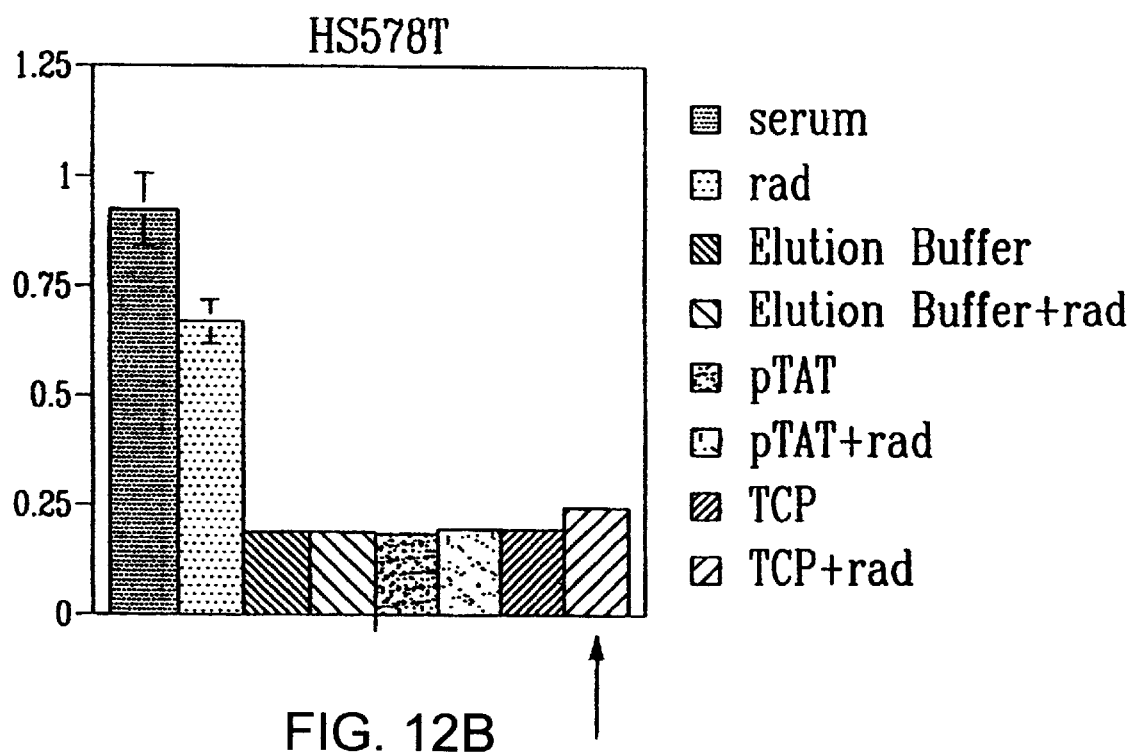
Figure 12C:
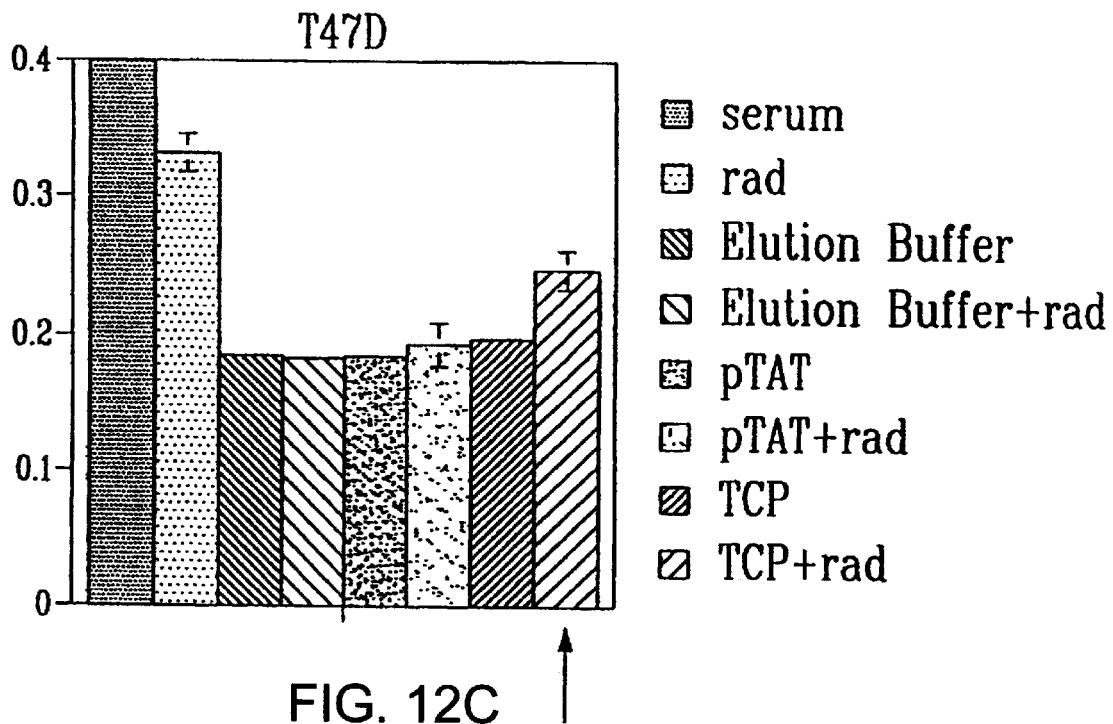
Figure 12D:
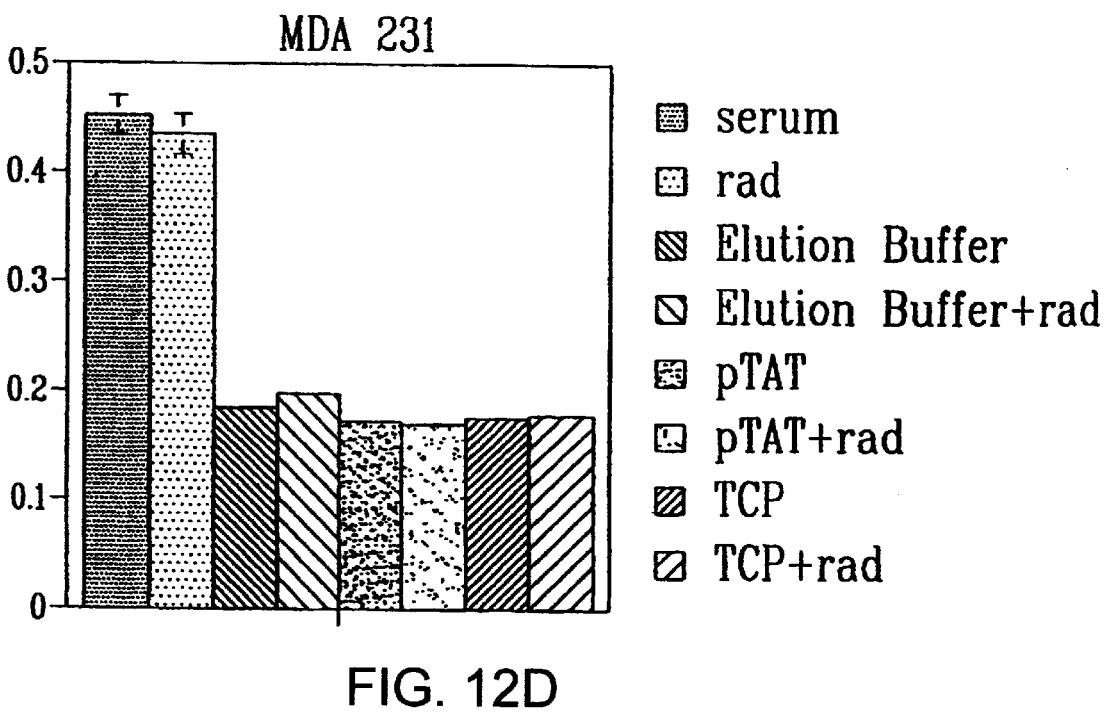
Figure 13:
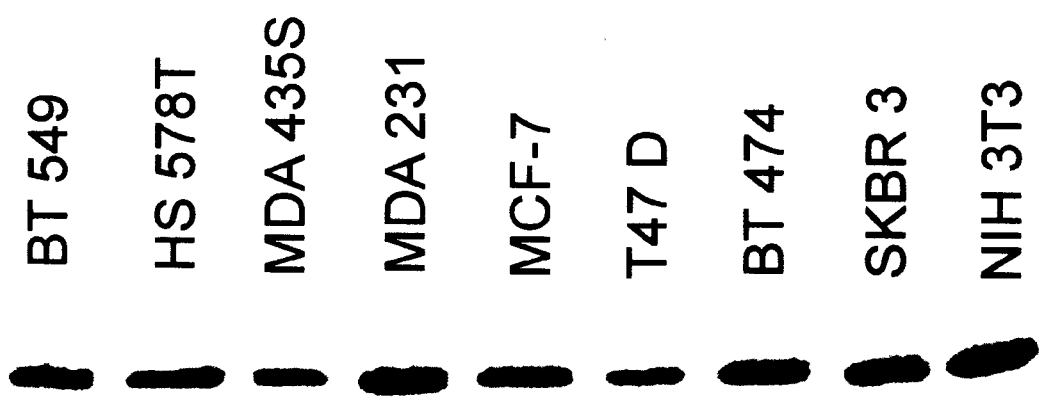
FIG. 13 illustrates the presence of significant TC-PTP proteins in human breast cancer cell lines.

Production of active TC-PTP in tat delivery system. In order to influence the sensitivity of mammalian cells towards DNA damage or to modulate its proliferation rate various mode of delivery must be developed to introduce either wildtype or dominant negative mutant of the TC-PTP. The tat-fusion protein system allows the direct entry of various peptides and proteins into mammalian cells. We have used this system to generate tat-TC-PTP wildtype (FIG. 9a) and C→S/D→N TC-PTP(FIG. 9c) to characterize the phenotypic consequences of their introduction into human cancer cells. The tat-wildtype TC-PTP fusion protein can be generated and purified in E. coli (FIG. 9b). The tat-wildtype TC-PTP fusion protein possesses significant phosphatase activity as assayed against a tyrosine phosphorylated peptides (FIG. 10). Entry of the tat-wtTC-PTP fusion protein into mammalian cells can be detected by western blotting with a anti TC-PTP monoclonal antibody (FIG. 11). Treatments of human breast cancer cells with the tat-wt-TC-PTP proteins provides to 3 (FIGS. 12a,b,c) out of 4 cell lines a detectable and significant protection against gamma irradiation, even though human breast cancer cell lines generally expressed high levels of TC-PTP (FIG. 13). These results demonstrate that introduction of TC-PTP proteins in mammalian cells can provide protection against DNA damaging agents.

Figure 14A:
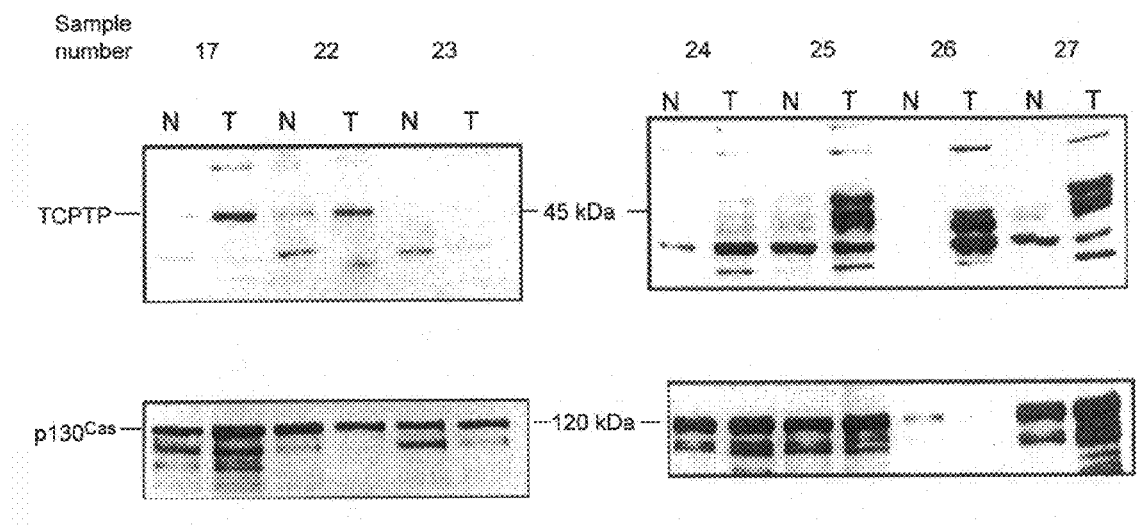
FIGS. 14A and 14B illustrate the presence in over 70% of colon cancer of increased levels of TC-PTP.
Figure 14B:
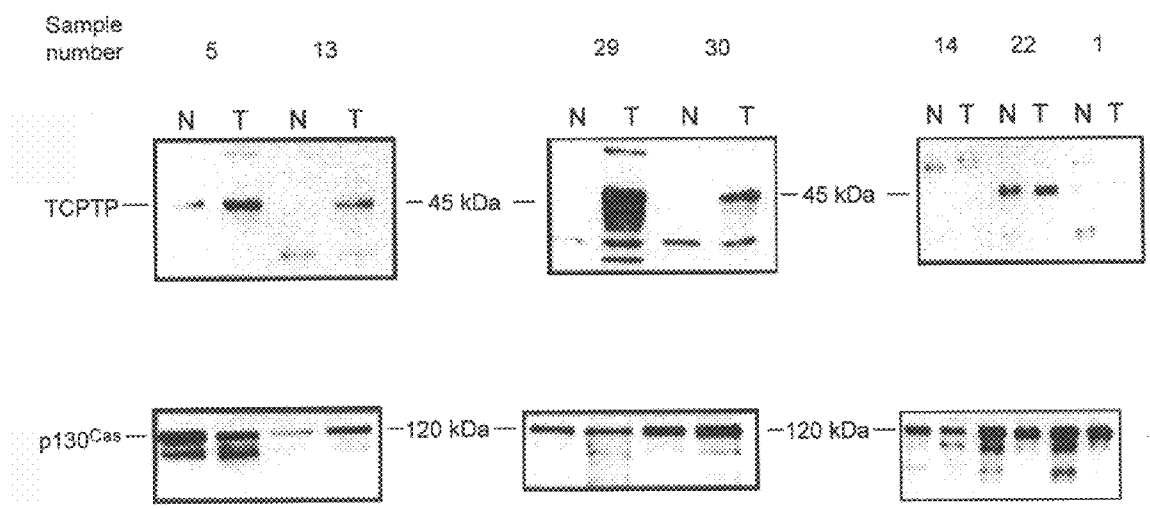

Expression of the TC-PTP in human colon cancer tissues. The existence of several human tumors that express increased levels of protooncogenes, such as c-myc, suggest that if the expression of TC-PTP is controlled by c-myc, then the expression level of IC-PTP would be increased in the relevant human cancer cells. In order to test the levels of TC-PTP expression in human tumors, we obtained 14 paired samples of normal and tumor tissues removed from human patients with colon cancer. Using p130cas expression to normalize the protein extract, we evaluated the level of TC-PTP by western blotting, and found increased TC-PTP protein in 10 out of 14 samples FIGS. 14A,B). These results suggest that TC-PTP could be playing a potential role in increasing cellular proliferation. Furthermore, as shown by the TC-PTP−/− cell lines, this enzyme is also a validated target for cancer therapy.

To address the cellular function of TC-PTP, we generated TC-PTP+/+ and TC-PTP−/− primary MEFs, as well as +/+, +/−, and −/− spontaneously immortalized fibroblast cell lines. Phenotypic analysis of these cells showed that TC-PTP is involved in the progression of G1 phase of the cell cycle, and in the cellular protection against DNA-damaging agents. The present data demonstrate that TC-PTP−/− cells present a reduced rate of proliferation, indicative of a positive role for TC-PTP in the regulation of cellular proliferation. The slow rate of growth is due to a longer G1 phase in the cell cycle in TC-PTP−/− cells. In support of this finding, we showed that cyclin E/Cdk2 complex and Rb are also affected in TC- PTP−/− cells. The expression of cyclin E is delayed in these cells, and consequently the activation of its partner, Cdk2 is also delayed. Furthermore the Rb protein remains in its inactive hypophosphorylated form for a longer time. Since one of the known mechanism of G1 phase regulation is exerted on the DNA repair machinery, we examined the response of the TC-PTP−/− cells to γ-irradiation. The viability of the TC-PTP deficient cells is dramatically reduced after irradiation, and the survival rate of TC-PTP−/− mice also indicates that in vivo the homozygous animals are highly sensitive to irradiation. Finally, we confirmed these results by directly assessing the level of single- and double-stranded break dependent DNA repair. This in vitro assay indicates that the DNA repair machinery from TC-PTP−/− cells is at least 10 times less active than the wild type counterpart.

It is known that proliferation control is primarily achieved in the G1 phase of the cell cycle. Among other signaling controls, the completion of G1 requires two protein complexes; cyclin D/Cdk4 in early G1 and cyclin E/Cdk2 in late G1. Their function is to phosphorylate the Rb protein to allow the transition between G1 to S-phase. Cyclin E/Cdk2 phosphorylates Rb in late G1. Once hyperphosphorylated, Rb is released from the complex with E2F. E2F then initiates the transcription of important genes for S phase. Due to our initial observations of slower proliferation and a long G1 phase in TC-PTP−/− cells, we tested the activation of one of the key complexes for the transition G1/S, cyclin E/Cdk2, which had a strong delay in its activation. The major consequence of delaying the activation of cyclin E/Cdk2 in TC-PTP−/− cells is reflected by the state of Rb phosphorylation that remains in a hypophosphorylated form for a much longer period of time, and thus delaying the transition from G1 to S phase. These findings imply the importance of TC-PTP as a positive effector in the upstream signaling that regulates the progression through the G1 phase. Furthermore, these results correlate well with a previous report that overexpression of the nuclear form of the TC-PTP causes cells to increase in their rate of proliferation (Radha et al. (1997) *FEBS letters* 409:33–36).

We also demonstrated that TC-PTP−/− cells are hypersensitive to γ-radiation. When we treated TC-PTP+/+ cells with a single dose of γ-radiation, the cells only suffered a small decrease in their survival, indicating that the DNA repair machinery is reactivated after certain period of time and the cells start to proliferate again. This phenomena does not happen in the TC-PTP−/− cells where the viability decreased dramatically after the treatment. The hypersensitivity of TC-PTP−/− cells treated with other DNA damaging agents like UV-C and MMS was similar to γ-radiation, suggesting that TC-PTP−/− exhibit a defect in the DNA repair machinery. Importantly, TC-PTP−/− mice also show a similar hypersensitivity to γ-radiation. Ionizing radiation is well known to generate not only double stranded breaks (DSB) in DNA, but also an increase in nuclear activity related to the repair machinery. To counteract double stranded breaks, mammalian cells possess two different mechanism of repair; homologous recombination (HR) and non homologous end joining (N-HEJ). In contrast to *S. cerevisiae*, NHEJ is the main mechanism of DSE repair in mammalian cells. When we examined the DNA repair machinery in vitro, we found that the ability of the TC-PTP−/− cells to repair DNA was defective in both HR and NHEJ mechanisms in -comparison to the TC-PTP+/+ cells. Since appropriate repair cannot be accomplished at a normal rate, the TC-PTP−/− cells may be forced by the G1 check point control to remain in this phase of the cell cycle in an attempt to eliminate DSB.

DNA damage by genotoxic stress is believed to activate several pathways. One of the first-events following DNA damage is the activation of DNA-PK enzyme by the presence of double stranded breaks. DNA-PK which is absent in SCID mice, is a heterocomplex of proteins that includes the Ku70 and 86 kDa subunit-proteins, and a large catalytic subunit DNA-PKcs. This enzyme appears to convey downstream signals via serine or threonine phosphorylation. Several substrates of DNA-PK have been identified that provide the connection between DNA-damage and cell cycle. Among others, DNA-PK physically associates and phosphorylates p53 following DNA damage, suggesting a mechanism by which p53 induced cell cycle inhibitor such as p16ink4A as well as the p21Wafl, that could be utilized for delaying the cell cycle in G1. In addition, evidence that p53 is directly involved in DNA repair was suggested by the finding that p53 also associates directly with the human Rad51 protein, a protein involved in both DNA recombination and repair. The fact that we identified a delay in the cell cycle from both primary cells, as well as in cell lines, suggests that TC-PTP function may be required even in a p53 defective environment. Pathways leading to activation of p21 that are p53 independent have also been reported. For example the BRCA1 dependent transactivation of p21 provides a means by which p53−/− cells could still be arrested or delayed at their G1 checkpoint, following DNA damage treatment.

The defect in both types of DNA repair machinery position the action of TC-PTP upstream or directly into the control of DNA repair enzymes. Its nuclear localization as well as its higher mRNA level of expression in late G1 also correlates well with such a modulating function. TC-PTP is a phosphotyrosine specific phosphatase. Hence, one must expect that such a modified substrate must also be involved in controlling DNA repair.

It is interesting to note that the tyrosine kinase c-Abl that has been found to modulate cellular responses to ionizing agents upstream of the repair machinery. For example, c-Abl−/− fibroblasts are more resistant to irradiation, an opposite phenotype to the TC PTP−/− cells. Following radiation damage c-Abl has been found to associate, and become a substrate of, both the Ataxia telangiectasia gene product ATM and by DNA-PK. One of the potential consequences of radiation-dependent, phosphorylation of c-Abl following its activation is to phosphorylate the Rad51 protein on tyrosine 54. Rad51 is a mammalian homologue of the bacterial recA protein that functions in DNA double stranded break repair. Importantly, the oncogene BCR-abl has been shown to phosphorylate p62dok, a substrate of the TC-PTP tyrosine phosphatase.

Another pathway involving the epidermal growth factor receptor (EGFR) tyrosine kinase has also been recently proposed to be implicated in radiation damage, with a specific interaction between the DNA-PK and the EGFR. This finding suggested that a crosstalk exists between mitotic signaling downstream of EGFR and DNA repair, that could play an important role in modulating cellular response to DNA damaging agent. The identification by substrate trapping of EGFR and the SHC adaptor proteins as in vitro substrates (Tiganis et al., 1998) could support the involvement of TC-PTP in this new pathway.

As shown by the TC-PTP−/− fibroblast phenotype, the generation of the TC-PTP−/− mice provides important information on the function of TC-PTP enzyme. In an earlier study, we reported that TC-PTP−/− mice die by 3–5 weeks, displaying an impaired proliferation in T and B splenocytes, as well as a total failure in bone marrow function due to the absence of bone marrow stromal cells. Since T and B cells maturation requires V(D)J recombination that involved DNA double strand breaks, this proliferation block may also be a manifestation of the inability of TC-PTP−/− lymphocytes to conduct non-homologous end joining (NHEJ) DNA repair. Interestingly SCID mice that are defective for DNA-PK and Ku80−/− mice both display immune and DNA repair deficiencies. Together, our data suggest that at least one major function of TC-PTP is to modulate the DNA-repair machinery in order to protect cells against DNA-damaging agents.

EXAMPLE 2

Modulation of TC-PTP Expression by c-myc

The effect of c-myc on the expression of a TC-PTP promoter-CAT reporter plasmid was examined, and it was found that c-myc was capable of upregulating transcription of TC-PTP in late-G1. Since, c-myc is universally induced by mitogens and most often down regulated by growth-inhibitory agents, experiments are performed to verify that TC-PTP is a transcriptional target of the c-myc transcription factor.

Deletion mutants are generated of the two putative myc binding sites, and tested in cotransfection assays with c-myc. DNA footprinting as well as electrophoretic mobility shift assay (EMSA) with the two binding sites is done to correlate modulation of expression with the deletion data, using extracts from cells in G0, in early G1 or in late G1. The expression of c-myc is tested for correlation with elevated expression of TC-PTP in transformed cells and tumor samples known to have elevated c-myc expression.

Promoter studies are published in Wee et al. (1999) *Gene* 237(2):351–60. In addition, the following experiments are performed.

A cis-actin S phase repressor. We have mapped the cis acting element responsible for the S phase repression between −2200 and −716 from the initiating AUG codon. Closer mapping using more defined mutants allows identification of the specific mechanism of repression controlling TC-PTP expression.

A binding site for PEA3 overlapping with the initiator element. The existence of competition between the transcription complex and the transcription factor PEA3 is examined.

The basis of high expression of TC-PTP in hematopoietic cells. Identification of the basis for upregulation of TC-PTP by hematopoietic specific transcription factors is performed using our library of promoter deletions linked to the CAT constructs, as described in Wee et al. 1999.

Expression constructs containing the sequences upstream of the TC-PTP gene are transfected into lymphoid jurkat cells, in order to determine if cis-acting regulatory elements required for high expression in hematopoietic, cells are contained within 2 Kbp of the transcription start site.

EXAMPLE 3

TC-PTP Posttranslational Processing

TC-PTP exists in two forms of 48 kDa and 45 kDa respectively, localized in the cytoplasm and nucleus. It has been proposed that murine TC-PTP is encoded by one mRNA, and that the different forms detected by SDS PAGE, are generated by post-translational processing. Interestingly, when TC-PTP proteins are examined during the cell-cycle, the 45 kDa appears to decrease in amount with the simultaneous increase in the 48 kDa form. In order to comprehend the function of TC-PTP, a solid biochemical understanding of these protein species is essential.
Phosphorylation To verify if these species are generated by phosphorylation, NIH-3T3 cell extract are treated by potato acid phosphatase, and the presence of shifts in the TC-PTP molecular weight is verified.

Immunoprecipitation (IP), with anti TC-PTP mAb is made from in vivo $^{32}$p orthophosphate labeled cells to verify the phosphorylation status of TC-PTP. Phosphoamino acid analysis of these $^{32}$P-labeled TC-PTP purified proteins is completed. The phosphorylation sites are mapped using peptide mapping by Fast Protein Liquid Chromatography (FPLC) and by the generation of ser/thr/tyr mutants. TC-PTP contains two putative ATM/DNA-PK phosphorylation sites SEQ ID NO: 1 (S/TQxxP) at thr 106 and ser 324, and CDK-like sites at ser 52 and ser 319. In vitro mutagenesis is carried out to confirm the functionality of a phosphorylation site. TC-PTP phosphorylation by ATM or DNA-PK is rapidly tested by immunoprecipitating these kinases from gamma irradiated cells, follow by in vitro phosphorylation of bacterially produced TC-PTP.

Other modifications can also be identified. Pulse chase labeling studies with $^{35}$S-methionine in NIH-3T3 is used to verify if the 45 kDa is modified into the 48 kDa by a cell cycle dependent modification. After purification of the 45 and 48 kDa bands, they are analyzed by tryptic peptide, and the carboxyl peptide is sequenced. The identification of each peptide is facilitated by the previous generation of a large number of TC-PTP deletion mutants.

EXAMPLE 4

Substrates and Associated Proteins of TC-PTP

The data presented in Example 1 demonstrates that p62dok associates reproducibly with the TC-PTP C-S mutant. The status of p62dok phosphorylation in +/+ and −/− fibroblasts following serum starvation and restimulation is established. To determine whether interaction with TC-PTP has repercussions on its association with p120ras-gap, p62dok is immunoprecipitated under conditions that protect protein-protein interactions. Using commercially available antibodies (anti p120ras-gap and anti-phosphotyrosine) western blotting is used to determine the amount of p120ras-gap brought down in the p62dok immunoprecipitation. It is expected that in TC-PTP−/− cells there is an increase in p62dok phosphorylation, and concurrent augmentation in the amount of associated p120ras-gap. C-ras activation status is followed in these cells using a GST-raf trapping assay to verify the effect of this complex on MAP kinase signaling. These experiments are repeated with hematopoietic cells of the knockout animals (i.e. spleen and thymus), and after stimuli, including gamma irradiation, U.V., and other DNA-damaging agents, to optimize the level of both TC-PTP and p62dok.

In addition to p62dok, a 25 kDa protein has been identified that shows increased tyrosine phosphorylation in gamma irradiated −/− fibroblast cells. The protein is identified using available antibodies against known proteins of the same molecular weight acting in DNA repair /cell cycle pathway. Purification of this protein is performed using affinity purification with anti-phosphotyrosine antibodies against irradiated TC-PTP knockout cell extracts, followed by other FPLC purification steps, and protein sequencing.

In order to verify if TC-PTP associates.with other non-substrate proteins, which could modify its enzymatic activity in vivo, An expression vector has been generated for initiating protein-protein interaction studies in the yeast two hybrid system. This hybrid protein contains the GAL4 DNA binding domain linked to the catalytically inactive carboxyl half of the enzyme. The fusion protein is expressed extremely well in yeast. Proteins that interact in the yeast system are be further tested for association with TC-PTP by in vitro far western blotting and in vivo by coimmunoprecipitation and immunofluorescence. To test for modulation of TC-PTP activity, TC-PTP catalytic activity assays are performed in presence of the identified binding partners. Alternatively, TC-PTP is immunoprecipitated from $^{35}$S methionine labeled normal or gamma irradiated wild type fibroblast cells, in conditions that preserve protein-protein interactions.

EXAMPLE 5

The Counteracting Function of c-abl Kinase and TC-PTP Phosphatase

As depicted in Table 2, the biological effects of TC-PTP and c-abl are antagonistic, not withstanding that both enzyme target the same p62dok substrate. Counteracting kinases and phosphatases modulate the proper balance of tyrosine phosphorylation.

TABLE 2

| PHENOTYPES | T-Cell PTP | c-Abl kinase |
| --- | --- | --- |
| catalytic activity | tyrosine phosphatase | tyrosine kinase |
| cellular localization | nuclear/cytoplasmic | nuclear/cytoplasmic |
| JNK pathway in knockout cells | always on | not activated by irradiation |
| radiosensitivity in knockout cells | increase sensitivity to radiation | decrease sensitivity to radiation |
| substrate | DOK | DOK, rad51, RNA polymerase |
| mouse knockout phenotype | lymphadenopathy | lymphopenia |

Cell lines that have a homozygous knockout in the abl gene are resistant to radiation. The radiation resistance is modified by expressing dominant negative TC-PTP (Cys to Ser, or D to A) mutants in these cells. A finding of increased sensitivity of these lines to irradiation will suggest that TC-PTP and c-abl enzymes act within the same signaling DNA repair pathway.

A double knockout of TC-PTP and c-abl is generated by breeding the two mouse lines. The phenotypic defect already reported for both animal models, including life span, lymphopenia, T and B cell proliferation, and splenomegaly are assessed. Double knockout fibroblast cell lines are isolated in-order to perform phenotypic studies in tissue culture, for radiation resistance, tyrosine phosphorylation patterns, and proliferation properties.

EXAMPLE 6

The Mechanism of Action of TC-PTP on the Cell Cycle and Apoptosis

TC-PTP+/– mice are bred to p53–/– mice. F1 mating of double heterozygous animals (p53+/– TC-PTP+/– X p53+/– TC-PTP+/–) should result in 1/16 of the progeny being double knockouts. Fibroblast lines are isolated from 14 to 16 day old embryos, and genotyped for both loci by Southern blotting. Phenotypic analysis of the double knockout animals is performed. Ionizing radiation sensitivity is verified in the different primary cell genotypes. An increased radioresistance for the double knockout fibroblasts is expected if the action of TC-PTP is through a p53 dependent pathway.

Other modulators of cell cycle, including p21 and p16 are examined in the TC PTP–/– and TC-PTP/p53 double knockout cells. p21WAF1 is tested in these studies. Using p21Waf1–/– cells and mice, it was shown that p21 can affect apoptosis, DNA repair, and cell cycle through both p53 dependent, and independent manner. These studies are complemented by overexpression studies with stable cell lines that overexpress TC-PTP.

The effect on cell cycle on the double mutants (abl–/– TC-PTP–/–; p53–/– TC-PTP–/–) fibroblasts is determined. The cells are tested by cell synchronization, FACS analysis and western blotting for cyclin complex proteins.

EXAMPLE 7

Involvement of TC-PTP in Initiation or Maintenance of Tumorigenicity

Overexpression of TC-PTP has been shown to cause an increase in cellular proliferation, suggesting an involvement in c-myc dependent increase in cellular proliferation. Increases in TC-PTP could contribute to the c-myc radiation resistance phenotype. As a first step to test these assumptions, we found that in 10 of 14 human cancer colon, TC-PTP protein level is increased, following protein normalization with the p130cas structural protein level (FIGS. 12a,b). These findings supports the putative function of TC-PTP in proliferation. An association with radioresistance is verified by correlating the radioresistance of tumors, or relapse from radiation therapy with levels of TC-PTP expression in colon cancer samples.

Matched samples of human adenocarcinoma and control normal adjacent tissues are tested. The increase in TC-PTP is correlated to a specific stage of cancer development by including samples that were pre-identified in their malignant stages. Data analysis is performed according to standard statistical analysis. Transgenic animals expressing ubiquitously high levels of TC-PTP through a CMV promoter are generated for further testing.

EXAMPLE 8

The Phenotypic Defect Occurring in TC-PTP–/– Mice

TC-PTP knockout mice display severe immunosuppression, and a phenotype that appear in acute GVHD in animals. GVHD is associated with a "cytokine storm" in which there is a pathologic production of inflammatory cytokines and other molecules, e,.g. nitric oxide (NO). We wish to further compare the TC-PTP–/– phenotype with that of GVHD mice.

TC-PTP knockout mice are compared to GVHD animals. The transcriptional up or down regulation of cytokines and growth factors is assayed using RNAse protection assay, using commercially available RNAse protection assay kits with multiprobes (up to 12 cytokines/kit) to investigate proinflammatory, inflammatory and hematopoietic factors. Western blotting and/or ELISA is used to confirm these findings at the, protein level.

The histological changes in the bone marrow stroma of TC-PTP–/– mice from shortly after birth until time of death are correlated with changes in growth factor production.

Endotoxins from Gram negative bacteria in the gut of GVHD mice initiate the septic shock-like symptoms that are associated with GVHD. It is therefore important to determine the role of microflora in the wasting, shock-like, phenotype that develops in TC-PTP–/– immunosuppressed mice.

TC-PTP gnotobiotic animals (germ free) are generated by fostering cesarean derived TC-PTP babies onto commercially available CDI gnotobiotic mothers. Absence of bacterial flora in the S gut has been shown to decrease dramatically the cytokine response in graft versus host phenomenon.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. An assay method comprising:

combining a candidate agent with a cell expressing TC-PTP;

combining said candidate with a cell comprising a heterozygous knockout of the endogenous TC-PTP genes and determining the effect of said candidate agent on cell cycle, wherein a delay in G1 phase in said cell expressing TC-PTP compared to said cell comprising a heterozygous knockout of the endogenous TC-PTP genes is indicative that said agent inhibits TC-PTP activity.

2. An assay method comprising:

combining a candidate agent in vitro with TC-PTP protein, and a protein substrate; and determining the effect of said candidate agent on phosphorylation of said substrate.

3. The method of claim 2, wherein said protein substrate is p62dok.

4. The method according to claim 1, wherein said cell expressing TC-PTP and said cell comprising a heterozygous knockout of the endogenous TC-PTP genes are cultured in vitro.

5. The method according to claim 1, wherein said TC-PTP is human TC-PTP.

6. The method according to claim 1, wherein said TC-PTP is mouse TC-PTP.

7. The method according to claim 1, wherein said TC-PTP is rat TC-PTP.

8. The method according to claim 1, wherein said effect on cell cycle is determined by the method of:

synchronizing each of said cells in G0;

culturing said synchronized cells for a defined period of time;

staining said cells with propidium iodide; and thereby analyzing the number of said cells that have progressed to G1 phase.

9. The method according to claim 2, wherein said TC-PTP is human TC-PTP.

10. The method according to claim 2, wherein said TC-PTP is mouse TC-PTP.

11. The method according to claim 2, wherein said TC-PTP is rat TC-PTP.

12. The method according to claim 2, wherein said protein substrate is labeled with $^{32}P$.

13. The method according to claim 10, wherein said determining step comprises immunoprecipitating said protein and quantitating the presence of $^{32}P$, wherein the presence of said $^{32}P$ is indicative that said protein substrate is phosphorylated.

14. An assay method comprising:

combining a candidate agent with a cell expressing TC-PTP;

combining said candidate with a cell comprising a heterozygous knock out of the endogenous TC-PTP genes and determining the effect of said candidate agent on DNA repair, wherein a decrease in recombination in said cell expressing TC-PTP compared to said cell comprising a heterozygous knockout of the endogenous TC-PTP genes is indicative that said agent inhibits TC-PTP activity.

15. The method according to claim 14, wherein said effect on DNA repair is determined by an in vitro recombination assay.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Consensus phosphorylation site
<221> NAME/KEY: VARIANT
<222> LOCATION: (1)...(1)
<223> OTHER INFORMATION: Xaa = S or T
<221> NAME/KEY: VARIANT
<222> LOCATION: (3)...(4)
<223> OTHER INFORMATION: Xaa = any amino acid

<400> SEQUENCE: 1

Xaa Gln Xaa Xaa Pro
1               5

<210> SEQ ID NO 2
<211> LENGTH: 14
<212> TYPE: PRT
<213> ORGANISM: Mus musculus

<400> SEQUENCE: 2

Ala Gly Ser Met Ala Gly Pro Met Ser Ala Thr Ile Glu Arg
1               5                   10
```